(12) United States Patent
Coric et al.

(10) Patent No.: US 12,364,687 B2
(45) Date of Patent: Jul. 22, 2025

(54) USE OF RILUZOLE ORAL DISINTEGRATING TABLETS FOR TREATING DISEASES

(71) Applicant: BIOHAVEN PHARMACEUTICAL HOLDING COMPANY LTD., New Haven, CT (US)

(72) Inventors: Vladimir Coric, Madison, CT (US); Robert Berman, New Haven, CT (US); Irfan Qureshi, Hackensack, NJ (US)

(73) Assignee: Biohaven Therapeutics Ltd., Tortola (VG)

( * ) Notice: Subject to any disclaimer, the term of this patent is extended or adjusted under 35 U.S.C. 154(b) by 1149 days.

(21) Appl. No.: 17/056,559

(22) PCT Filed: May 26, 2019

(86) PCT No.: PCT/US2019/034081
§ 371 (c)(1),
(2) Date: Nov. 18, 2020

(87) PCT Pub. No.: WO2019/231865
PCT Pub. Date: Dec. 5, 2019

(65) Prior Publication Data
US 2022/0218673 A1 Jul. 14, 2022

Related U.S. Application Data

(60) Provisional application No. 62/677,018, filed on May 27, 2018, provisional application No. 62/739,774, filed on Oct. 1, 2018.

(51) Int. Cl.
| A61K 31/428 | (2006.01) |
| A61K 9/00 | (2006.01) |
| A61K 9/20 | (2006.01) |
| A61P 21/00 | (2006.01) |
| A61P 25/28 | (2006.01) |

(52) U.S. Cl.
CPC .......... *A61K 31/428* (2013.01); *A61K 9/0056* (2013.01); *A61K 9/006* (2013.01); *A61K 9/2018* (2013.01); *A61K 9/2063* (2013.01); *A61K 9/2095* (2013.01); *A61P 21/00* (2018.01); *A61P 25/28* (2018.01)

(58) Field of Classification Search
CPC .............................. A61K 31/428; A61P 25/28
See application file for complete search history.

(56) References Cited

U.S. PATENT DOCUMENTS

| 6,245,791 B1 * | 6/2001 | Bohme ................ A61K 31/428 |
| | | 514/367 |
| 9,511,045 B2 | 12/2016 | Busserolles et al. |
| 9,725,427 B2 | 8/2017 | Smith et al. |
| 2004/0076666 A1 | 4/2004 | Green et al. |
| 2010/0093655 A1 | 4/2010 | Achour et al. |

FOREIGN PATENT DOCUMENTS

| WO | 2015195989 A1 | 12/2015 | |
| WO | 2016081466 A1 | 5/2016 | |
| WO | WO-2016081472 A1 * | 5/2016 | ........... A61K 31/428 |

OTHER PUBLICATIONS

International Search Report dated Nov. 5, 2019 issued for the corresponding application PCT/US2019/034081 (2 pages).
Written Opinion dated Nov. 5, 2019 issued for the corresponding application PCT/US2019/034081 (5 pages).
International Preliminary Report on Patentability dated Nov. 5, 2019 issued for the corresponding application PCT/US2019/034081 (6 pages).
Jose Marques Lopes "Bioequivalence Study of Sublingual BHV-0223 Shows Positive Results as Rilutek Substitute" published online at www.alsnewstoday.com on Jan. 11, 2018 (7 pages).

* cited by examiner

*Primary Examiner* — Kevin E Weddington

(57) ABSTRACT

Disclosed are methods of treating a disease in a patient in need thereof, comprising administering to the patient a pharmaceutical composition comprising a therapeutically effective amount of riluzole, or a pharmaceutically acceptable salt thereof, in the form of an oral solid molded fast-dispersing dosage form. Pharmaceutical compositions and kits are also disclosed.

4 Claims, 8 Drawing Sheets

USE OF RILUZOLE ORAL DISINTEGRATING TABLETS FOR TREATING DISEASES

CROSS-REFERENCE TO RELATED APPLICATIONS

This application is a national stage application under 35 U.S.C. § 371 of International Application No. PCT/US2019/034081, filed May 26, 2019, which claims priority to U.S. Provisional Application No. 62/677,018 filed May 27, 2018 and U.S. Provisional Application No. 62/739,774 filed Oct. 1, 2018, and all the benefits accruing therefrom under 35 U.S.C. § 119, the disclosure of each of which applications is herein incorporated by reference in its entirety.

FIELD OF THE INVENTION

The present invention relates to the use of riluzole oral disintegrating tablets and their use in treating diseases.

BACKGROUND OF THE INVENTION

Glutamate is a predominant excitatory neurotransmitter responsible for regulating signaling in normal brain function. While research on glutamate signaling has been primarily focused on the central nervous system (CNS), other investigations have highlighted their functional role in peripheral tissues. See, e.g., Skerry T, Genever P, Glutamate signaling in non-neuronal tissues. Trends Pharmacol Sci 2001, 22:174-181 and Frati C, Marchese C, Fisichella G, Copani A, Nasca M R, Storto M, Nicoletti F, Expression of functional mGlu5 metabotropic glutamate receptors in human melanocytes. J Cell Physiol 2000, 183:364-372.

Glutamate can exert its signaling abilities by acting on glutamate receptors, which are located on the cell surface. Glutamate receptors exist as either ionotropic receptors (iGluRs) or metabotropic glutamate receptors (mGluRs). iGluRs are ligand-gated ion channels, which include N-methyl-d-aspartate (NMDA) receptors and non-NMDA receptors [α-amino-3-hydroxy-5-methyl-4-isoxazolepropionic acid (AMPA) receptors] (iGluR1-4) and kainite (KA) subfamilies (iGluR5-7, KA1, and KA2). mGluRs are domain receptors that mediate their signal by coupling to Guanosine triphosphate (GTP)-binding proteins (G-proteins) and stimulate second messengers such as inositol 1,4,5-triphosphate (IP3), diacylglycerol (DAG), and cyclic adenosine monophosphate (cAMP). Various mGluR subtypes have been identified and grouped according to their sequence homology, pharmacologic response, and intracellular second messengers. Upon binding of the ligand, Group I receptors, which are comprised of mGluR1 and mGluR5, couple via G. to phospholipase C (PLC) leading to the formation of IP3 and DAG. Group II comprises mGluR2 and mGluR3, and Group III comprises mGluR4, mGluR6, mGluR7 and mGluR8. Both Group II and III are negatively coupled via $G_{i/o}$ to adenyl cyclase leading to CAMP formation. See, e.g., Teh J, Chen S, Metabotropic glutamate receptors and cancerous growth, WIREs Membr Transp Signal 2012, 1:211-220. doi: 10.1002/wmts.21, 2011 WILEY-VCH Verlag Gmbh & Co. KGaA, Weinheim. Volume 1, March/April 2012.

Glutamate can also be transported. Glutamate transporters have been cloned from the mammalian central nervous system. Two are expressed predominantly in glia [glial glutamate and aspartate transporter (GLAST) and glial glutamate transporter (GLT)] and three in neurons [EAAC1, excitatory amino acid transporter (EAAT)4 and EAAT5]. See, e.g., Seal, R, Amara, S, (1999) Excitatory amino acid transporters: a family in flux. Annu. Rev. Pharmacol. Toxicol. 39:431-456. Further information concerning glutamate transport can be found in the literature. See, e.g., Meldrum B, Glutamate as a Neurotransmitter in the Brain: Review of Physiology and Pathology, J. Nutr. 130: 1007S-1015S, 2000.

Glutamate can also be metabolized. Glutamate metabolism reactions can be catalyzed by enzymes that are regulated by activators and inhibitors. For instance, conversion of L-glutamate to N-acetyl L-glutamate in presence of N-acetylglutamate synthase (NAGS) is activated by L-arginine and inhibited by succinate, coenzyme A, N-acetyl-L-aspartate and N-acetyl-L-glutamate. See, e.g., Shigesada K, Tatibana M, N-acetylglutamate synthetase from rat-liver mitochondria. Partial purification and catalytic properties. Eur J Biochem. 1978; 84:285-291. doi: 10.1111/j.14321033.1978. tb12167.x. Similarly, glutamine to glutamate conversion can be catalyzed by enzymes, which include glutaminase (GLS/GLS2), phosphoribosyl pyrophosphate amidotransferase (PPAT) and glutamine-fructose-6-phosphate transaminase (GFPT1 and GFPT2). See, e.g., Holmes E, Wyngaarden J, Kelley W, Human glutamine phosphoribosylpyrophosphate amidotransferase. Two molecular forms interconvertible by purine ribonucleotides and phosphoribosylpyrophosphate. J Biol Chem 1973; 248: 6035-6040, and Hu C, et al. Molecular enzymology of mammalian Delta1-pyrroline-5-carboxylate synthase. Alternative Splice donor Utilization Generates Isoforms with Different Sensitivity to Ornithine Inhibition. J Biol Chem. 1999; 274:6754-6762. doi: 10.1074/jbc.274.10.6754.

Glutamine, which serves as a precursor of glutamate is known to protect the body from nutrient depletion, oxidative stress and tumor stress. See, e.g., Shanware N, et al., Glutamine: pleiotropic roles in tumor growth and stress resistance. J Mol Med (Berl) 2011; 89:229-236. doi: 10.1007/s0010901107319. Reports have shown that ammonia released from glutamine by the action of glutaminases regulates autophagy in cancer cells through a process known as glutaminolysis. See, e.g., Eng C, et al., (2010) Ammonia derived from glutaminolysis is a diffusible regulator of autophagy. Sci Signal 3: ra31. In cancer cells, glutaminolysis may serve as a fuel for cell growth and proliferation through the synthesis of fatty acids, nucleotides and amino acids. See, e.g., Benjamin D, et al., Global profiling strategies for mapping dysregulated metabolic pathways in cancer. Cell Metab. 2012; 16:565-577. doi: 10.1016/j.cmet.2012.09.013. Expression of glutaminase may be regulated by the transcription factor, c-Myc, which in turn regulates cell proliferation and cell death in human prostate cancer cells. See, e.g., Gao P, et al., c-Myc suppression of miR23a/b enhances mitochondrial glutaminase expression and glutamine metabolism. Nature. 2009; 458:762-765. doi: 10.1038/nature07823. In brain tumors such as gliomas, it has been shown that glioma cells may release excess glutamate into the extracellular space resulting in tumor-related epilepsy or seizures. See, e.g., Simon M, von Lehe M, Glioma-related seizures: glutamate is the key. Nat Med. 2011; 17:1190-1191. doi: 10.1038/nm.2510. There are also suggestions that glutamate release promotes cell proliferation, cell invasion and tumor necrosis in glioblastoma. See, e.g., Schunemann D, et al., Glutamate promotes cell growth by EGFR signaling on U87MG human glioblastoma cell line. Pathol Oncol Res. 2010; 16:285-293. doi: 10.1007/s1225300992234. Further information concerning glutamate and glutamine metabolism can be found in the literature. See, for example, Yelamanchi S., et al., A pathway map of glutamate metabolism, J Cell Commun Signal. 2016 March: 10 (1): 69-76. Doi10.1007/s12079-015-0315-5, and Chen L and Hengmin C, Targeting Glutamine Induces Apoptosis: A Cancer Therapy Approach, Int. J. Mol. Sci. 2015, 16, 22830-22855; doi: 10.3390/ijms160922830.

Amyotrophic lateral sclerosis (ALS) is a progressive neurodegenerative motor neuron disease that affects nerve cells in the brain and the spinal cord. The disease belongs to a group of disorders known as motor neuron diseases, which are characterized by the gradual degeneration and death of motor neurons. ALS affects up to 20,000 individuals in the United States and typically presents in patients with painless muscle weakness, trouble swallowing and muscle atrophy that ultimately progresses to paralysis, impaired breathing and death.

Riluzole (6-(trifluoromethoxy)benzothiazol-2-amine) is a pharmaceutical which has been used for treatment of ALS and was approved by the United States Food and Drug Administration (FDA) in 1995. However, while patients have benefited from the availability of riluzole, there have not been further clinical improvements or advances in ALS riluzole therapeutics for a considerable time. Riluzole itself has pharmacokinetic and pharmaceutic limitations that have restricted its broader clinical application. Riluzole tablets have about 60% bioavailability, attributed to high first-pass metabolism in the liver that is thought to be mediated via metabolism by the heterogeneously expressed CYP1A2 enzyme. This metabolic route is also thought to contribute to the high pharmacokinetic variability associated with riluzole. In addition, riluzole is associated with reduced exposure when taken with meals, or a negative food effect, resulting in the guidance to take riluzole within a period of fasting (one hour before or two hours after a meal) for each of two daily doses. In addition, riluzole has dose-dependent effects on liver function tests that necessitate periodic liver function test monitoring and is associated with transient liver transaminase elevations. At riluzole daily doses of 100 mg, drug discontinuation is required in 2% to 4% of subjects. The drug substance of riluzole itself has other intrinsic limitations that complicate the ability to produce non-tablet formulations, including very low solubility in water, poor oral palatability, pH dependent chemical stability and intense oral numbness if administered directly to the oral mucosa.

Recently, riluzole has been shown to have other clinical benefits. For example, orally administered riluzole dosed twice a day at a total dose of 100 mg per day may relieve or treat neuropsychiatric symptoms and disorders, such as mood, anxiety disorder, refractory depression, obsessive-compulsive anxiety and the like. See, e.g., Riluzole Augmentation in Treatment-refractory Obsessive-compulsive Disorder, Yale University (2016) Retrieved from https://clinicaltrials.gov/ct2 (Identification No. NCT00523718). Also, there is some indication that riluzole may have anti-cancer effects. See, e.g., Riluzole in Treating Patients With Stage III or Stage IV Melanoma That Cannot Be Removed by Surgery, Rutgers University (2013) Retrieved from https://clinicaltrials.gov/ct2 (Identification No. NCT00866840).

Despite the benefits that patients have received through the treatment of diseases by the administration of riluzole, improvements are desired. For example, an early symptom in many patients with ALS is difficulty swallowing, which makes it especially challenging for ALS patients to swallow traditional riluzole tablets. ALS patients may benefit from a fast-dissolving tablet that does not require swallowing or administration of liquids. Also, riluzole is associated with dose-dependent liver function increases attributable to high dose loads and extensive liver metabolism. With a sublingually absorbed form of riluzole, first-pass liver metabolism may be mitigated and lower doses of riluzole may be needed to be administered, thereby reducing potential risk for hepatic enzyme elevations.

SUMMARY OF THE INVENTION

The present invention is directed to methods of treating diseases in patients in need thereof, comprising administering to the patient a pharmaceutical composition comprising a therapeutically effective amount of riluzole, or a pharmaceutically acceptable salt thereof, in the form of an oral solid molded fast-dispersing dosage form in order to provide an $AUC_{0-t}$ of from about 80-125% of about 740000 hr*pg/mL, wherein the dosage of riluzole in the oral solid molded fast dispersing tablet is from 50 to 90% of the dosage of riluzole in a conventional tablet in order to provide an $AUC_{0-t}$ of about 740000 hr*pg/mL.

In one aspect of the invention, the dosage of riluzole in the oral solid molded fast dispersing tablet is from 70 to 85% of the dosage of riluzole in a conventional tablet in order to provide an $AUC_{0-t}$ of about 740000 hr*pg/mL. In one aspect of the invention, the dosage of riluzole in the oral solid molded fast dispersing tablet is from 70 to 85% of the dosage of riluzole in a conventional tablet in order to provide an $AUC_{0-t}$ of about 740000 hr*pg/mL. In one aspect of the invention, the dosage of riluzole in the oral solid molded fast dispersing tablet is about 40 mg.

In one aspect of the invention, the disease is ALS.

In one aspect of the invention, there is provided a pharmaceutical composition comprising a therapeutically effective amount of riluzole, or a pharmaceutically acceptable salt thereof, in the form of an oral solid molded fast-dispersing dosage form in order to provide an $AUC_{0-t}$ of from about 80-125% of about 740000 hr*pg/mL, wherein the dosage of riluzole in the oral solid molded fast dispersing tablet is from 50 to 90%, more preferably 70 to 85%, and most preferably about 80% of the dosage of riluzole in a conventional tablet in order to provide an $AUC_{0-t}$ of about 740000 hr*pg/mL.

In one aspect of the invention, the pharmaceutical composition contains from about 50-70 wt % riluzole, about 10-30 wt % fish gelatin, about 10-20 wt % of a filler, and 0.1-5.0 wt % of a flavorant. In one aspect of the invention, the filler is mannitol.

In one aspect of the invention, there is provided a kit for treating a disease in a patient, the kit comprising:
(a) a pharmaceutical composition comprising a therapeutically effective amount of riluzole, or a pharmaceutically acceptable salt thereof in the oral solid molded fast dispersing tablet;
(b) instructions for administering the pharmaceutical composition; wherein the therapeutically effective amount provides an $AUC_{0-t}$ of from about 80-125% of 740000 (hr*pg/mL).

In some aspects of the invention, a pharmaceutically acceptable salt, ester or prodrug of riluzole, as further described herein, is substituted for riluzole as the active ingredient.

DESCRIPTION OF THE DRAWINGS

These and/or other aspects will become apparent and more readily appreciated from the following description of the embodiments, taken in conjunction with the accompanying drawings, in which.

DETAILED DESCRIPTION OF THE INVENTION

Figure 1:
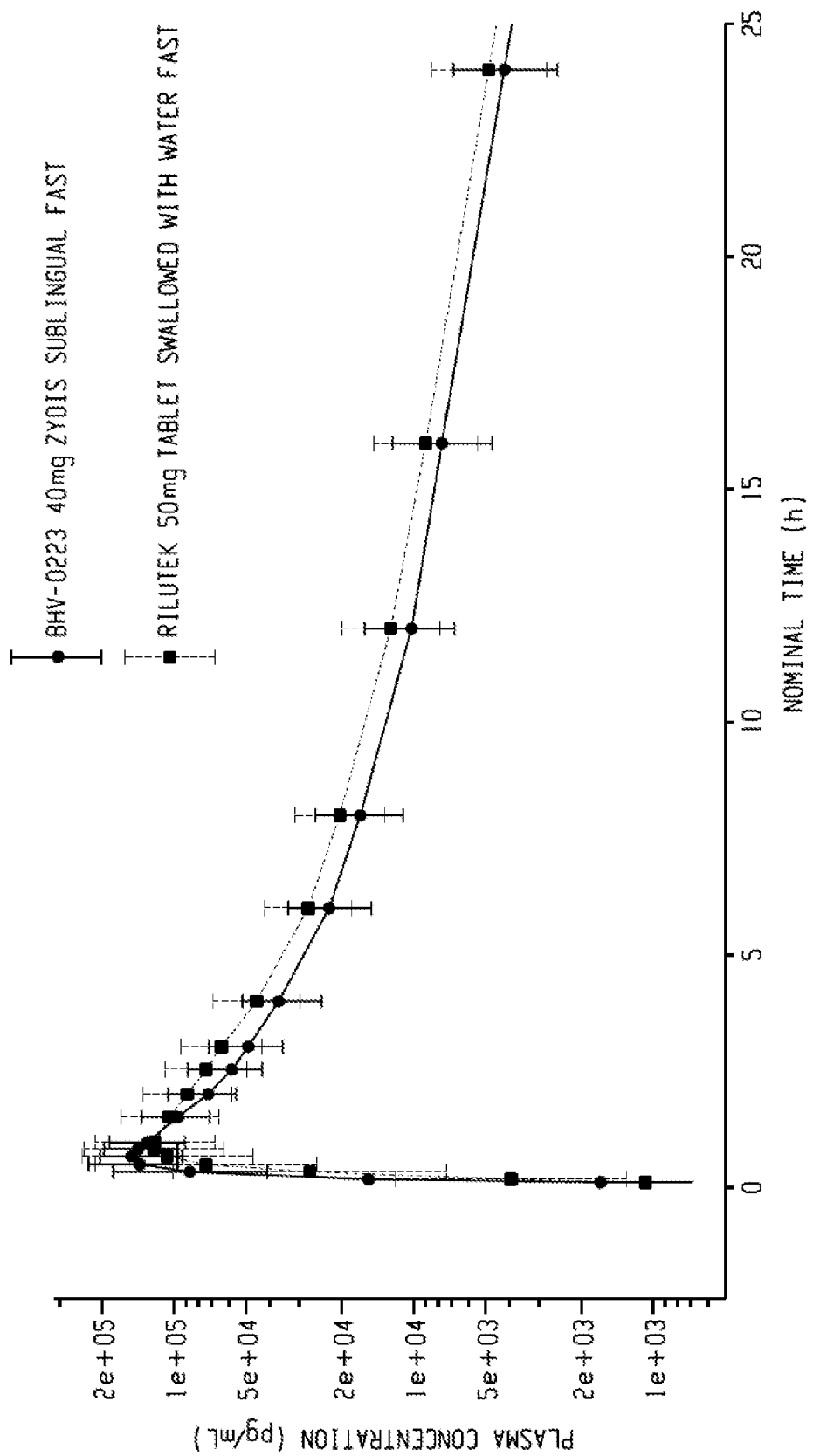
FIG. 1 illustrates riluzole plasma concentrations over time for BHV-0233 and Rilutek under fasted conditions.

The following detailed description is provided to aid those skilled in the art in practicing the present invention. Those of ordinary skill in the art may make modifications and variations in the embodiments described herein without departing from the spirit or scope of the present disclosure. Unless otherwise defined, all technical and scientific terms used herein have the same meaning as commonly understood by one of ordinary skill in the art to which this disclosure belongs. The terminology used in the description is for describing particular embodiments only and is not intended to be limiting.

As used in this application, except as otherwise expressly provided herein, each of the following terms shall have the meaning set forth below. Additional definitions are set forth throughout the application. In instances where a term is not specifically defined herein, that term is given an art-recognized meaning by those of ordinary skill applying that term in context to its use in describing the present invention.

The articles "a" and "an" refer to one or to more than one (i.e., to at least one) of the grammatical object of the article unless the context clearly indicates otherwise. By way of example, "an element" means one element or more than one element.

The term "about" refers to a value or composition that is within an acceptable error range for the particular value or composition as determined by one of ordinary skill in the art, which will depend in part on how the value or composition is measured or determined, i.e., the limitations of the measurement system. For example, "about" can mean within 1 or more than 1 standard deviation per the practice in the art. Alternatively, "about" can mean a range of up to 10% or 20% (i.e., ±10% or ±20%). For example, about 3 mg can include any number between 2.7 mg and 3.3 mg (for 10%) or between 2.4 mg and 3.6 mg (for 20%). Furthermore, particularly with respect to biological systems or processes, the terms can mean up to an order of magnitude or up to 5-fold of a value. When particular values or compositions are provided in the application and claims, unless otherwise stated, the meaning of "about" should be assumed to be within an acceptable error range for that particular value or composition.

The term "administering" refers to the physical introduction of a composition comprising a therapeutic agent to a subject, using any of the various methods and delivery systems known to those skilled in the art. For example, routes of administration for riluzole can include buccal, intranasal, ophthalmic, oral, osmotic, parenteral, rectal, sublingual, topical, transdermal, or vaginal. Administering can also be performed, for example, once, a plurality of times, and/or over one or more extended periods and can be a therapeutically effective dose or a subtherapeutic dose.

The term "AUC" (area under the curve) refers to a total amount of drug absorbed or exposed to a subject. Generally, AUC may be obtained from mathematical method in a plot of drug concentration in the subject over time until the concentration is negligible. The term "AUC" (area under the curve) could also refer to partial AUC at specified time intervals (as may be the case with sublingual absorption which would increase AUC at earlier time intervals).

The term "cancer" refers to a broad group of various diseases characterized by the uncontrolled growth of abnormal cells in the body. Unregulated cell division and growth results in the formation of malignant tumors that invade neighboring tissues and can also metastasize to distant parts of the body through the lymphatic system or bloodstream. "Cancer" includes primary, metastatic and recurrent cancers as well as a precancerous condition, i.e., a state of disordered morphology of cells that is associated with an increased risk of cancer. The term "cancer" includes, but is not limited to, the following proliferative diseases: Acute Lymphoblastic Leukemia (ALL), Acute Myeloid Leukemia (AML), Adrenocortical Carcinomas, Childhood cancers, AIDS-Related Cancers, Kaposi Sarcoma, AIDS-Related Lymphoma, Primary CNS Lymphoma, Anal Cancer, Astrocytomas, Atypical Teratoid/Rhabdoid Tumor, Basal Cell Carcinoma, Skin Cancer (Nonmelanoma), Bile Duct Cancer, Bladder Cancer, Bone Cancer, Ewing Sarcoma Family of Tumors, Osteosarcoma and Malignant Fibrous Histiocytoma, Brain Stem Glioma, Atypical Teratoid/Rhabdoid Tumor, Embryonal Tumors, Germ Cell Tumors, Craniopharyngioma, Ependymoma, Breast Cancer, Bronchial Tumors, Burkitt Lymphoma, Non-Hodgkin Lymphoma, Carcinoid Tumor, Gastrointestinal Carcinoma, Cardiac (Heart) Tumors, Primary Lymphoma, Cervical Cancer, Cholangiocarcinoma, Chordoma, Chronic Lymphocytic Leukemia (CLL), Chronic Myelogenous Leukemia (CML), Chronic Myeloproliferative Neoplasms, Colon Cancer, Colorectal Cancer, Craniopharyngioma, Cutaneous T-Cell Lymphoma, Mycosis Fungoides and Sézary Syndrome, Ductal Carcinoma In Situ (DCIS), Embryonal Tumors, Endometrial Cancer, Ependymoma, Esophageal Cancer, Esthesioneuroblastoma, Extracranial Germ Cell Tumor, Extragonadal Germ Cell Tumor, Eye Cancer, Intraocular Melanoma, Retinoblastoma, Fallopian Tube Cancer, Fibrous Histiocytoma of Bone, Malignant, and Osteosarcoma, Gallbladder Cancer, Gastric (Stomach) Cancer, Gastrointestinal Carcinoid Tumor, Gastrointestinal Stromal Tumors (GIST), Germ Cell Tumor, Ovarian, Testicular, Gestational Trophoblastic Disease, Glioma, Hairy Cell Leukemia, Head and Neck Cancer, Hepatocellular (Liver) Cancer, Histiocytosis, Langerhans Cell, Hodgkin Lymphoma, Hypopharyngeal Cancer, Islet Cell Tumors, Pancreatic Neuroendocrine Tumors, Kaposi Sarcoma, Kidney, Renal Cell, Langerhans Cell Histiocytosis, Laryngeal Cancer, Leukemia, Acute Lymphoblastic (ALL), Acute Myeloid (AML), Chronic Lymphocytic (CLL), Chronic Myelogenous (CML), Hairy Cell, Lip and Oral Cavity Cancer, Liver Cancer (Primary), Lung Cancer, Non-Small Cell, Small Cell, Lymphoma, Hodgkin, Non-Hodgkin, Macroglobulinemia, Waldenström, Male Breast Cancer, Melanoma, Merkel Cell Carcinoma, Mesothelioma, Metastatic Squamous Neck Cancer with Occult Primary, Midline Tract Carcinoma Involving NUT Gene, Mouth Cancer, Multiple Endocrine Neoplasia Syndromes, Multiple Myeloma/Plasma Cell Neoplasm, Mycosis Fungoides, Myelodysplastic Syndromes, Myelodysplastic/Myeloproliferative Neoplasms, Myelogenous Leukemia, Chronic (CML), Myeloid Leukemia, Acute (AML) Myeloma, Multiple, Myeloproliferative Neoplasms, Nasal Cavity and Paranasal Sinus Cancer, Nasopharyngeal Cancer, Neuroblastoma, Non-Hodgkin Lymphoma, Non-Small Cell Lung Cancer, Oral Cancer, Oral Cavity Cancer, Lip and Oropharyngeal Cancer, Osteosarcoma and Malignant Fibrous Histiocytoma of Bone, Ovarian Cancer, Low Malignant Potential Tumor, Pancreatic Cancer, Pancreatic Neuroendocrine Tumors (Islet Cell Tumors), Papillomatosis, Paraganglioma, Paranasal Sinus and Nasal Cavity Cancer, Parathyroid Cancer, Penile Cancer, Pharyngeal Cancer, Pheochromocytoma, Pituitary Tumor, Plasma Cell Neoplasm/Multiple Myeloma, Pleuropulmonary Blastoma, Pregnancy and Breast Cancer, Primary CNS Lymphoma, Primary Peritoneal Cancer, Prostate Cancer, Rectal Cancer, Renal Cell (Kidney) Cancer, Renal Pelvis and Ureter, Transitional Cell Cancer, Retinoblastoma, Rhabdomyosarcoma, Salivary Gland Cancer, Rhabdomyosarcoma, Uterine, Small Intestine Cancer, Soft Tissue Sarcoma, Squamous Cell Carcinoma, Squamous Neck Cancer with Occult Primary, Metastatic, Stomach (Gastric) Cancer, T-Cell Lymphoma, Testicular Cancer, Throat Cancer, Thymoma and Thymic Carcinoma, Thyroid Cancer, Transitional Cell Cancer of the Renal Pelvis and Ureter, Unknown Primary, Ureter and Renal Pelvis, Transitional Cell Cancer, Urethral Cancer, Uterine Cancer, Endometrial, Uterine Sarcoma, Vaginal Cancer, Vulvar Cancer, Waldenström Macroglobulinemia, and Wilms Tumor.

The term "$C_{max}$" refers to a maximum concentration of a drug in blood, serum, a specified compartment or test area of a subject between administration of a first dose and administration of a second dose. The term $C_{max}$ could also refer to dose normalized ratios if specified.

The term "dosing interval," refers to the amount of time that elapses between multiple doses of a pharmaceutical composition disclosed herein being administered to a subject. Dosing interval can thus be indicated as ranges.

The term "disease" means abnormalities in systemic functions resulting from a pathophysiological response to external or internal factors, including disorders, conditions and syndromes, e.g. a disruption to the normal or regular functions in the body or a part of the body, a collection or set of signs and symptoms that characterize or suggest a particular disease or an abnormal state of physical or mental health that interferes with the activities or feeling of well-being.

The term "dosing frequency" refers to the frequency of administering doses of a pharmaceutical composition disclosed herein in a given time. Dosing frequency can be indicated as the number of doses per a given time, e.g., once a week or once in two weeks.

The term "effective amount" refers to that amount which is sufficient to effect an intended result. The effective amount will vary depending on the subject and disease state being treated, the severity of the affliction and the manner of administration, and may be determined routinely by one of ordinary skill in the art.

The term "fixed dose" with regard to a pharmaceutical composition refers to two or more different therapeutic agents in a single composition are present in the composition in particular (fixed) ratios with each other. In some embodiments, the fixed dose is based on the weight (e.g., mg) of the therapeutic agents. In some embodiments, the ratio of the therapeutic agents is at least about 1:1, about 1:2, about 1:3, about 1:4, about 1:5, about 1:6, about 1:7, about 1:8, about 1:9, about 1:10, about 1:15, about 1:20, about 1:30, about 1:40, about 1:50, about 1:60, about 1:70, about 1:80, about 1:90, about 1:100, about 1:120, about 1:140, about 1:160, about 1:180, about 1:200, about 200:1, about 180:1, about 160:1, about 140:1, about 120:1, about 100:1, about 90:1, about 80:1, about 70:1, about 60:1, about 50:1, about 40:1, about 30:1, about 20:1, about 15:1, about 10:1, about 9:1, about 8:1, about 7:1, about 6:1, about 5:1, about 4:1, about 3:1, or about 2:1 mg of the first therapeutic agent to mg of the second therapeutic agent.

The terms "in combination with" and "in conjunction with" refer to administration of one treatment modality in addition to another treatment modality. As such, "in combination with" or "in conjunction with" refers to administration of one treatment modality before, during, or after administration of the other treatment modality to the subject.

The term "pharmaceutically acceptable salt" refers to a salt form of one or more of the therapeutic agents described, e.g., riluzole, herein which are presented to increase the solubility of the compound in the gastric or gastroenteric juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids and bases well known in the pharmaceutical art.

The term "prodrug" refers to a precursor of a drug which may be administered in an altered or less active form. The prodrug may be converted into the active drug form in physiological environments by hydrolysis or other metabolic pathways. A discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press.

The term "sublingual administration" refers to a route of administrating a chemical agent or a drug by placing thereof under a tongue of a subject.

The terms "subject" and "patient" refer any human or nonhuman animal. The term "nonhuman animal" includes, but is not limited to, vertebrates such as nonhuman primates, sheep, dogs, and rodents such as mice, rats and guinea pigs. In some embodiments, the subject is a human. The terms, "subject" and "patient" are used interchangeably herein.

The term, "subtherapeutic dose" refers a dose of a therapeutic agent that is lower than the usual or typical dose of the therapeutic agent when administered alone for the treatment of a disease (e.g., cancer).

The terms "therapeutically effective amount", "therapeutically effective dosage" and "therapeutically effective dose" of an agent (also sometimes referred to herein as a "drug") refers to an effective amount of the agent that, when used alone or in combination with another agent, protects a subject against the onset of a disease or promotes disease regression evidenced by a decrease in severity of disease symptoms, an increase in frequency or duration of disease symptom-free periods, or a prevention of impairment or disability due to the disease affliction.

The term "$T_{max}$" refers to a time or period after administration of a drug when the maximum concentration ($C_{max}$) is reached in blood, serum, a specified compartment or test area of a subject.

The term "treatment" refers to any treatment of a condition or disease in a subject and may include: (i) preventing the disease or condition from occurring in the subject which may be predisposed to the disease but has not yet been diagnosed as having it; (ii) inhibiting the disease or condition, i.e., arresting its development; relieving the disease or condition, i.e., causing regression of the condition; or (iii) ameliorating or relieving the conditions caused by the disease, i.e., symptoms of the disease. Treatment could be used in combination with other standard therapies or alone. Treatment or "therapy" of a subject also includes any type of intervention or process performed on, or the administration of an agent to, the subject with the objective of reversing, alleviating, ameliorating, inhibiting, slowing down or preventing the onset, progression, development, severity or recurrence of a symptom, complication or condition, or biochemical indicia associated with a disease.

The term "weight based dose" refers to a dose that is administered to a patient is calculated based on the weight of the patient. For example, when a patient with 60 kg body weight requires 3 mg/kg of a therapeutic agent, one can administer the appropriate amounts of the therapeutic agent (i.e., 180 mg).

Actual dosage levels of the active ingredient or ingredients in the pharmaceutical compositions of the present invention can be varied so as to obtain an amount of the active ingredient which is effective to achieve the desired therapeutic response for a particular patient, composition, and mode of administration, without being unduly toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

Riluzole is currently available in the market as RILUTEK® (riluzole) is available from Sanofi-Aventis, Bridgewater, NJ and has the structure shown below.

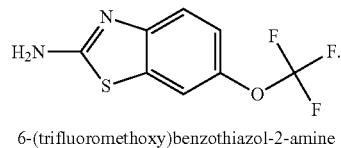

6-(trifluoromethoxy)benzothiazol-2-amine

Riluzole, as used in accordance with the present invention, may be present as isotopically labeled forms of compounds detailed herein. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, Cl and I. Various isotopically labeled compounds of the present disclosure, for example those into which radioactive isotopes such as $^3$H, $^{13}$C and $^{14}$C are incorporated, are provided. Such isotopically labeled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of subjects (e.g. humans). Also provided for isotopically labeled compounds described herein are any pharmaceutically acceptable salts, or hydrates, as the case may be.

In some variations, the compounds disclosed herein may be varied such that from 1 to "n" hydrogens attached to a carbon atom is/are replaced by deuterium, in which "n" is the number of hydrogens in the molecule. Such compounds may exhibit increased resistance to metabolism and are thus useful for increasing the half life of the compound when administered to a subject. See, for example, Foster, "Deuterium Isotope Effects in Studies of Drug Metabolism", Trends Pharmacol. Sci. 5 (12): 524-527 (1984). Such compounds are synthesized by means well known in the art, for example by employing starting materials in which one or more hydrogens have been replaced by deuterium.

Deuterium labeled or substituted therapeutic compounds of the disclosure may have improved drug metabolism and pharmacokinetics (DMPK) properties, relating to absorption, distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An 18F labeled compound may be useful for PET or SPECT studies. Isotopically labeled compounds of this disclosure can generally be prepared by carrying out the procedures known to those skilled in the art by substituting a readily available isotopically labeled reagent for a non-isotopically labeled reagent. It is understood that deuterium in this context is regarded as a substituent in the compounds provided herein.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as 'H' or "hydrogen", the position is understood to have hydrogen at its natural abundance isotopic composition.

The term "riluzole prodrug" refers to a compound which is a derivative from riluzole with modification therein. A riluzole prodrug may also refer to a compound that is metabolized into an active form of riluzole by the body.

Certain preferred riluzole prodrugs have the structure:

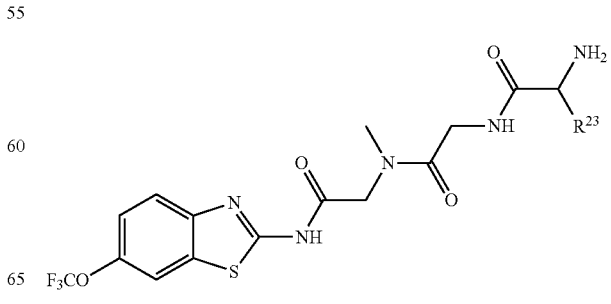

including enantiomers, diastereomers, hydrates, solvates, pharmaceutically acceptable salts, and complexes thereof, wherein:

$R_{23}$ is selected from the group consisting of H, $CH_3$, $CH_2CH_3$, $CH_2CH_2CH_3$, $CH_2CCH$, $CH(CH_3)_2$, $CH_2CH(CH_3)_2$, $CH(CH_3)$ $CH_2CH_3$, $CH_2OH$, $CH_2OCH_2Ph$, $CH_2CH_2OCH_2Ph$, $CH(OH)$ $CH_3$, $CH_2Ph$, $CH_2$ (cyclohexyl), $CH_2$ (4-OH-Ph), $(CH_2)_4NH_2$, $(CH_2)_3NHC(NH_2)$ NH, $CH_2$ (3-indole), $CH_2$ (5-imidazole), $CH_2CO_2H$, $CH_2CH_2CO_2H$, $CH_2CONH_2$, and $CH_2CH_2CONH_2$.

One especially preferred prodrug of riluzole is troriluzole, which has the following formula:

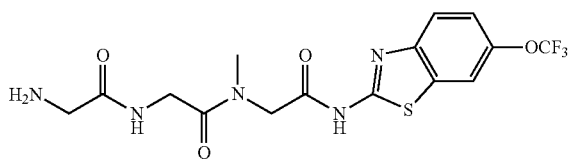 [SMILES: CN(CC(=O)Nc1nc2ccc(OC(F)(F)F)cc2s1)C(=O)CNC(=O)CN]

Prodrugs of riluzole are described, for example, in U.S. patent application Ser. No. 14/385,551, U.S. patent application Ser. No. 14/410,647, PCT Application Ser. No. PCT/US2016/019773 and PCT Application Ser. No. PCT/US2016/019787. Sublingual formulations of riluzole that provide stability and excellent properties are described in PCT Application Ser. No. PCT/US2015/061106 and PCT Application Ser. No. PCT/US2015/061114.

The therapeutically effective dose of riluzole suitable for use in accordance with the present invention depends on a variety of factors, including, for example, the disease or disorder to be treated, the subject to be treated inclusive of the age, sex, weight and general health condition thereof. In this regard, precise amounts of the agent(s) for administration will depend on the judgment of the practitioner. In determining the effective amount of riluzole to be administered in the treatment or reducing of the conditions associated with the symptoms and disorders, the physician may evaluate clinical factors including symptoms severity or progression of the disorder. The effective amount of the treatment will vary depending on the subject and disease state being treated, the severity of the affliction and the manner of administration, and may be determined routinely by one of ordinary skill in the art. Dosages of riluzole include, for example, for treating a disease or symptoms may be at or below about 400 mg/day, at or below about 300 mg/day, at or below about 150 mg/day, at or below about 120 mg/day, at or below about 80 mg/day, at or below about 40 mg/day, at or below about 20 mg/day, at or below about 10 mg/day, at or below about 5 mg/day, or at or below about 1 mg/day. The dosing frequency may be, for example, once per month, once per week, once per day, twice per month, twice per week, twice per day or another frequency.

The pharmaceutical compositions of the present invention comprising riluzole typically also include other pharmaceutically acceptable carriers and/or excipients such as binders, lubricants, diluents, coatings, disintegrants, barrier layer components, glidants, coloring agents, solubility enhancers, gelling agents, fillers, proteins, co-factors, emulsifiers, solubilizing agents, suspending agents and mixtures thereof. A skilled artisan in the art would know what other pharmaceutically acceptable carriers and/or excipients could be included in the formulations according to the invention. The choice of excipients would depend on the characteristics of the compositions and on the nature of other pharmacologically active compounds in the formulation. Appropriate excipients are known to those skilled in the art (see Handbook of Pharmaceutical Excipients, fifth edition, 2005 edited by Rowe et al., McGraw Hill).

Examples of pharmaceutically acceptable carriers that may be used in preparing the pharmaceutical compositions of the present invention may include, but are not limited to, fillers such as sugars, including lactose, sucrose, mannitol, or sorbitol; cellulose preparations such as maize starch, wheat starch, rice starch, potato starch, gelatin, gum tragacanth, methyl cellulose, hydroxypropyl methyl-cellulose, sodium carboxymethylcellulose, polyvinyl-pyrrolidone (PVP), talc, calcium sulphate, vegetable oils, synthetic oils, polyols, alginic acid, phosphate buffered solutions, emulsifiers, isotonic saline, pyrogen-free water and combinations thereof. If desired, disintegrating agents may be combined as well, and exemplary disintegrating agents may be, but not limited to, cross-linked polyvinyl pyrrolidone, agar, or alginic acid or a salt thereof such as sodium alginate. In an aspect of the invention, the flavoring agent is selected from mint, peppermint, berries, cherries, menthol and sodium chloride flavoring agents, and combinations thereof. In an aspect of the invention, the sweetener is selected from sugar, sucralose, aspartame, acesulfame, neotame, and combinations thereof.

Preferably, the pharmaceutical compositions containing riluzole are suitable to be administered sublingually. PCT Application No. PCT/US2015/061106 and PCT Application No. PCT/US2015/061114 describe a sublingual formulation of riluzole. When riluzole is prepared as a sublingual formulation, the sublingually administered chemical agent or the drug can diffuse into capillaries through mucous membrane under the tongue, and then enter venous circulation of the subject. As such, sublingual administration may have advantages over oral administration as a conventional tablet by allowing for direct or faster entry to venous circulation, without risks of degradation in gastrointestinal tract, alteration by drug metabolism in liver and the like. Alternatively, the sublingual formulations of the present invention containing riluzole may also be administered such that they are permitted to dissolve on the top of the tongue.

A sublingual formulation useful in the present invention comprises an effective amount of riluzole or pharmaceutically acceptable salts, solvates, anomers, enantiomers, hydrates or prodrugs thereof. The formulation provides sufficient solubility for riluzole to be incorporated into the sublingual formulation and sublingually delivered. The formulation is preferably presented as an oral disintegrating tablet (ODT) of riluzole. In general, the excipients, including mannitol and gelatin, are blended, solubilized with water and deaerated before being mixed with the active pharmaceutical ingredient (API), riluzole, which has been milled separately. Particle size of the API (D50) is less preferably than about 2 microns. The mixture is lyophilized by flash freezing and then freeze-dried. The effective amount of riluzole for the sublingual formulation useful in the present invention to achieve a therapeutically effective dose may be less than that of orally administered agent. Moreover, a therapeutically effective dose of the sublingual formulation of riluzole may be about 1 to 95%, about 50 to 90%, about 70 to 85%, e.g., about 80% of that of the orally administered agent in a conventional tablet, e.g., RILUTEK. For example, an ODT formulation of the present invention may contain about 40 mg of riluzole and have bioequivalence to a 50 mg tablet of RILUTEK.

In one aspect of the invention the pharmaceutical compositions are prepared in oral solid molded fast-dispersing dosage form, such as described in U.S. Pat. No. 9,192,580, issued Nov. 24, 2015.

The phrase "fast-dispersing dosage form" refers to compositions which disintegrate or disperse within 1 to 60 seconds, preferably 1 to 30 seconds, more preferably 1 to 10 seconds and particularly 2 to 8 seconds, after being placed in contact with a fluid. The fluid is preferably that found in the oral cavity, i.e., saliva, as with oral administration. In accordance with the present invention, an ODT is a fast-dispersing dosage form.

In a preferred embodiment, the compositions of the invention are solid fast-dispersing dosage forms comprising a solid network of the active ingredient, rimegepant, and a water-soluble or water-dispersible carrier containing fish gelatin. Accordingly, the carrier is inert towards the active ingredient. The network is obtained by subliming solvent from a composition in the solid state, the composition comprising the active ingredient and a solution of the carrier in the solvent. The dosage forms according to the invention can be prepared according to the process disclosed in Gregory et al., U.K. U.S. Pat. No. 1,548,022 using fish gelatin as the carrier. Accordingly, an initial composition (or admixture) comprising the active ingredient and a solution of the fish gelatin carrier in a solvent is prepared followed by sublimation. The sublimation is preferably carried out by freeze drying the composition. The composition can be contained in a mold during the freeze-drying process to produce a solid form in any desired shape. The mold can be cooled using liquid nitrogen or solid carbon dioxide in a preliminary step prior to the deposition of the composition therein. After freezing the mold and composition, they are next subjected to reduced pressure and, if desired, controlled application of heat to aid in sublimation of solvent. The reduced pressure applied in the process can be below about 4 mm Hg, preferably below about 0.3 mm Hg. The freeze dried compositions can then be removed from the mold if desired or stored therein until later use.

When the process is used with active ingredients and fish gelatin as the carrier, a solid fast-dispersing dosage form is produced having the advantages associated with the use of fish gelatin described herein. Generally, fish gelatin is categorized as being from cold water and warm water fish sources and as being of the gelling or non-gelling variety. The non-gelling variety of fish gelatin, in comparison to gelling fish gelatin and bovine gelatin, contains lower proline and hydroxyproline amino acid content, which are known to be associated with cross-linking properties and gelling ability. Non-gelling fish gelatin can remain at solution concentrations of up to about 40% as well as in temperatures as low as 20° C. In one aspect of the invention, the fish gelatin used in accordance with the invention is preferably obtained from cold water fish sources and is the non-gelling type of fish gelatin. More preferably, in one aspect of the invention, the non-hydrolyzed form of non-gelling fish gelatin is used. In an alternative embodiment, spray-dried non-hydrolyzed non-gelling fish gelatin can be used. Fish gelatins suitable for use in the invention are commercially available.

The compositions according to the invention can also contain, in addition to the active ingredient arid fish gelatin carrier, other matrix forming agents and secondary components. Matrix forming agents suitable for use in the present invention include materials derived from animal or vegetable proteins, such as other gelatins, dextrins and soy, wheat and *psyllium* seed proteins; gums such as acacia, guar, agar, and 10 xanthan; polysaccharides; alginates; carboxymethylcelluloses; carrageenans; dextrans; pectins; synthetic polymers such as polyvinylpyrrolidone; and polypeptide/protein or polysaccharide complexes such as gelatin-acacia complexes.

Other materials which may also be incorporated into the fast-dissolving compositions of the present invention include sugars such as mannitol, dextrose, lactose, galactose, and trehalose; cyclic sugars such as cyclodextrin; inorganic salts such as sodium phosphate, sodium chloride and aluminum silicates; and amino acids having from 2 to 12 carbon atoms such as glycine, L-alanine, L-aspartic acid, L-glutamic acid, L-hydroxyproline, L-isoleucine, L-leucine and L-phenylalanine. One or more matrix forming agents may be incorporated into the solution or suspension prior to solidification (freezing). The matrix forming agent may be present in addition to a surfactant or to the exclusion of a surfactant. In addition to forming the matrix, the matrix forming agent may aid in maintaining the dispersion of any active ingredient within the solution of suspension. This is especially helpful in the case of active agents that are not sufficiently soluble in water and must, therefore, be suspended rather than dissolved. Secondary components such as preservatives, antioxidants, surfactants, viscosity enhancers, coloring agents, flavoring agents, pH modifiers, sweeteners or taste-masking agents may also be incorporated into the fast-dissolving compositions. Suitable coloring agents include red, black and yellow iron oxides and FD & C dyes such as FD&C Blue No. 2 and FD&C Red No. 40 available from Ellis & Everard. Suitable flavoring agents include mint, raspberry, licorice, orange, lemon, grapefruit, caramel, vanilla, cherry and grape flavors and combinations of these. Suitable pH modifiers include the edible acids and bases, such as citric acid, tartaric acid, phosphoric acid, hydrochloric acid, maleic acid and sodium hydroxide. Suitable sweeteners include, for example, sucralose, aspartame, acesulfame K and thaumatin. Suitable taste-masking agents include, for example, sodium bicarbonate, ion exchange resins, cyclodextrin inclusion compounds, adsorbates or microencapsulated actives.

In a preferred aspect of the invention, the fast-dissolving compositions comprise from about 50-70 wt % riluzole, about 10-30 wt % fish gelatin, about 10-20 wt % of one or more fillers, and 0.1-5.0 wt % of one or more flavorants.

A representative example of a dosage form in accordance with the present invention is as follows:

| Component | Function | Strength 40 mg | |
|---|---|---|---|
| | | Quantity per unit (mg) | % (w/w) |
| Riluzole, micronized | Active Ingredient | 30-40 | 50-70 |
| Gelatin | Binder | 5-15 | 15-25 |
| Mannitol | Filler | 5-15 | 10-20 |
| Docusate sodium | Disintegrant | 0.1-0.5 | 0.1-2 |
| Sucralose, micronized | Flavorant | 0.1-2.0 | 0.1-5 |
| Mint flavor | Flavorant | 0.1-2.0 | 0.1-5 |
| Purified water[1] | Carrier | 100-300 | N/A |
| Total | | | 100.00 |

[1]Purified water is removed during processing

The clinical or therapeutic effect of the riluzole sublingually formulated may have an improved pharmacokinetic profile for the pharmaceutical agent as measured by standard testing parameters. When the riluzole is administered sublingually, one or more of the $T_{max}$, $C_{max}$ and AUC of the drug may be improved compared to the same dose of the orally administered version of the same compound. For example, the sublingual formulation of the riluzole may have a greater $C_{max}$ than the orally administered riluzole to provide a therapeutically beneficial effect. The sublingual formulation of the riluzole may have an earlier or lesser $T_{max}$ than the orally administered riluzole to provide a therapeutically beneficial effect and in some instances, a more rapid therapeutic effect. Alternatively, the sublingual formulation of the riluzole may have a greater AUC per milligram of the agent than the orally administered riluzole.

Identifying the subject in need of such treatment can be in the judgment of the subject or a health care professional and can be subjective (e.g., opinion) or objective (e.g., measurable by a test or diagnostic method). The identified subject may be an animal or human in need thereof, particularly a human. Such treatment will be suitably administered to subjects, particularly humans, suffering from the disease.

The therapeutic effect of the pharmaceutical compositions of the present invention may be evident to occur within about a few minutes to about an hour after administration thereof. In particular, the therapeutic effect may begin within about 1 minute, within about 2 minutes, within about 3 minutes, within about 4 minutes, within about 5 minutes, within about 6 minutes, within about 7 minutes, within about 8 minutes, within about 9 minutes, within about 10 minutes, within about 11 minutes, within about 12 minutes, within about 13 minutes, within about 14 minutes, within about 15 minutes, within about 16 minutes, within about 17 minutes, within about 18 minutes, within about 20 minutes, within about 60 minutes, or within about 90 minutes after administration.

The therapeutic effect on the symptoms of the disease may be maintained for about 1 hour, for about 2 hours, for about 3 hours, for about 4 hours, for about 5 hours, for about 6 hours for about 7 hours, for about 8 hours, for about 9 hours, for about 10 hours, for about 12 hours, for about 14 hours, for about 16 hours, for about 18 hours, for about 20 hours, for about 22 hours, for about 24 hours, for about 2 days, or for about 3 days or more after administration thereof. In the treatment of some diseases, the therapeutic effect may provide temporary relief from symptoms associated with the disease. In the treatment of some diseases, the therapeutic effect may provide permanent relief from the disease.

The diseases which may be treated in accordance with the present invention include any diseases in which the administration of riluzole may have a therapeutic or sub-therapeutic effect. For example, the disease may be a neuropsychiatric disorder or symptom. In particular, the neuropsychiatric disorder may be anxiety disorders, generalized anxiety disorder, panic disorder, social anxiety, mood disorders,-cognitive disorders, schizophrenia, dementia, agitation, apathy, anxiety, psychoses, post-traumatic stress disorders, irritability, disinhibition, learning disorders, memory loss, personality disorders, bipolar disorders, obsessive-compulsive disorders, autism, Rett syndrome, eating disorders, conduct disorders in DSM-5 and or combinations thereof. The disease state may also include neurodegenerative disorders, pain disorders, ALS, cerebellar ataxia, other ataxia, Huntington's disease, Parkinson's disease, supranuclear palsy, frontotemporal dementia, frontotemporal lobar degeneration, delirium, Alzheimer's disease, mild cognitive impairment, mild cognitive impairment due to Alzheimer's disease, drug addiction, tinnitus, and mental retardation.

In addition, the neuropsychiatric symptom may be anxiety, depression, stress, fatigue, feelings of panic, fear, uneasiness, problems in sleeping, cold or sweaty hands and/or feet, mood liability, mania, impaired concentration or attention, cognitive problems, obsessions, compulsions, repetitive behaviors, aggression, social phobias or impairments, stage fright, shortness of breath, heart palpitations, an inability to be still and calm, dry mouth, numbness or tingling in the hands or feet, nausea, muscle tension, dizziness apathy, elation, disinhibition, irritability, wandering, irritable bowel, belly pain, belly discomfort, diarrhea, change in bowel habits, abdominal bloating, abdominal gas, abdominal bloating, constipation or combinations thereof.

In one aspect of the invention, the disease is cancer and riluzole is a component of combination therapy, e.g., with an immunotherapeutic agent, a chemotherapeutic agent, radiation therapy or other cancer treatment.

In some embodiments, a method may comprise administering to a subject one or more additional agent(s) simultaneously or sequentially with the riluzole. The selection of the additional agents to be administered in combination with riluzole are dependent, among other things, on the disease being treated, e.g., cancer, the selection of which can be made by one of ordinary skill in the art, e.g., a physician.

Cancer immunotherapy includes approaches that enhance anti-tumor immune responses by adoptive-transfer of activated effector cells, immunization against relevant antigens, or providing non-specific immune-stimulatory agents such as cytokines. Cancer immunotherapy also includes immune checkpoint pathway inhibitors that have provided new immunotherapeutic approaches for treating cancer, including, for example, inhibitors that target the Programmed Death-1 (PD-1) receptor and block the inhibitory PD-1/PD-1 ligand pathway and the Cytotoxic T-Lymphocyte Antigen-4 (CTLA-4) receptor.

PD-1 is a key immune checkpoint receptor expressed by activated T and B cells and mediates immunosuppression. Inhibition of the PD-I/PD-LI interaction mediates potent antitumor activity in preclinical models (See, e.g., U.S. Pat. Nos. 8,008,449 and 7,943,743), and the use of antibody inhibitors of the PD-I/PD-LI interaction for treating cancer has been studied in clinical trials. See, e.g., Topalian S, et al., Targeting the PD-1/B7-H1 (PD-L1) pathway to activate antitumor immunity. *Curr Opin Immunol* (2012) 24:207-212; Pardoll D, The blockade of immune checkpoints in cancer immunotherapy. *Nature Reviews Cancer* (2012) 12:252-264.

Nivolumab (marketed by Bristol-Myers Squibb Company, Princeton, NJ, USA under the tradename "OPDIVO", also known as 5C4, BMS-936558, MDX-1106, or ONO-4538) is a fully human IgG4 (S228P) PD-1 immune checkpoint inhibitor antibody that selectively prevents interaction with PD-1 ligands (PD-L1 and PD-L2), thereby blocking the down-regulation of antitumor T-cell functions. See, e.g., U.S. Pat. No. 8,008,449; Wang et al. (2014); see also http://www.cancer.gov/drugdictionary?cdrid=695789 (last accessed: Apr. 25, 2017). Pembrolizumab (marketed by Merck & Co., Inc, Whitehouse Station, NJ, USA under the tradename "KEYTRUDA", also known as lambrolizumab, and MK-3475) is a humanized monoclonal IgG4 antibody directed against human cell surface receptor PD-1. Pembrolizumab is described, for example, in U.S. Pat. Nos. 8,354,509 and 8,900,587; see also http://www.cancer.gov/drugdictionary?cdrid=539833 (last accessed: Apr. 25, 2017).

Ipilimumab (marketed by Bristol-Myers Squibb Company, Princeton, NJ, USA under the tradename "YERVOY") is a fully human, IgG1 monoclonal antibody that blocks the binding of CTLA-4 to its B7 ligands, thereby stimulating T cell activation and improving overall survival in patients with advanced melanoma. Ipilimumab is described, for example, in U.S. Pat. No. 6,984,720; see also http://www.cancer.gov/drugdictionary?cdrid=38447 (last accessed: Apr. 25, 2017).

Examples of other therapeutic approaches to cancer with immunology targeting anti-cancer agents include other antibodies that target a variety of receptors, as well as peptides, proteins, small molecules, adjuvants, cytokines, oncolytic viruses, vaccines, bi-specific molecules and cellular therapeutic agents. See, e.g., Ott P, et al. Combination immunotherapy: a road map Journal for ImmunoTherapy of Cancer (2017) 5:16 doi: 10.1186/s40425-017-0218-5, and Hoos A, Development of immuno-oncology drugs—from CTLA4 to PD1 to the next generations, *Nat Rev Drug Discov.* 2016 April; 15 (4): 235-47. doi: 10.1038/nrd.2015.35.

Dosage regimens for treating cancer can be determined by one skilled in the art. Typically, dosing regimens are adjusted to provide the optimum desired response, e.g., a maximal therapeutic response and/or minimal adverse effects. For example, in the administration of an anti-PD-1 antibody, as a monotherapy or in combination with another agent, the dosage can range from about 0.01 to about 20 mg/kg, about 0.1 to about 10 mg/kg, about 0.1 to about 5 mg/kg, about 1 to about 5 mg/kg, about 2 to about 5 mg/kg, about 7.5 to about 12.5 mg/kg, or about 0.1 to about 30 mg/kg of the subject's body weight. The dosing schedule is typically designed to achieve exposures that result in sustained receptor occupancy (RO) based on typical pharmacokinetic properties of an agent, e.g., antibody. An exemplary immune therapy treatment regime for treating cancer entails administration about once per week, once about every 2 weeks, once about every 3 weeks, once about every 4 weeks, once about a month, once about every 3-6 months or longer. In certain embodiments, an anti-PD-1 antibody such as NIVOLUMAB is administered to the subject once about every 2 weeks. In other embodiments, the antibody is administered once about every 3 weeks. The dosage and scheduling can change during a course of treatment. In some embodiments, the antibody treatment, or any combination treatment disclosed herein for treating cancer, is continued for at least about 1 month, at least about 3 months, at least about 6 months, at least about 9 months, at least about 1 year, at least about 18 months, at least about 24 months, at least about 3 years, at least about 5 years, or at least about 10 years. In one aspect of the invention, the patient is treated with a riluzole ODT, or a salt or prodrug of riluzole, as an adjunctive treatment in the treatment of cancer.

In one aspect, the invention also provides kits for use in the instant methods. Kits can include one or more containers comprising a pharmaceutical composition described herein and instructions for use in accordance with any of the methods described herein. Generally, these instructions comprise a description of administration of the pharmaceutical composition to treat, ameliorate or prevent a disease, e.g., ALS, according to any of the methods described herein. The kit may, for example, comprise a description of selecting an individual suitable for treatment based on identifying whether that individual has ALS. The instructions are typically provided in the form of a package insert, or label, in accordance with the requirements of the regulatory having authority over the jurisdiction where the pharmaceutical composition is to be provided to patients.

EXAMPLES

The following examples illustrate the invention and are not intended to limit the scope of the invention. In some examples, abbreviations are used which are known to those skilled in the art or are readily accessible from the documents cited in the examples.

Example 1 a Phase 1 Study to Evaluate the Bioequivalence Between BHV-0223 (Riluzole 40 mg Sublingual Orally Disintegrating Tablet) and Rilutek 50 mg Tablet and to Evaluate the Food-Effect of BHV-0223 in Normal Healthy Volunteers The study is sometimes referred herein as BHV0223-102. The primary elements of the protocol used in the study are as follows.

OBJECTIVES

Primary Objectives

To compare the rate and extent of absorption of BHV-0223 administered sublingually as 1×40 mg ODT versus RILUTEK administered orally as 1×50 mg tablet in NHV under fasting conditions.
To evaluate the effect of food on the pharmacokinetics of BHV-0223, when administered as a single 40 mg sublingual dose in NHV.

Secondary Objective

To assess the safety and tolerability of BHV-0223.
To assess rate of sublingual absorption of crushed riluzole tablets (50 mg RILUTEK) in subset of NHVs.

Exploratory Objective

To explore systemic metabolite profiles of riluzole when administered as oral RILUTEK and sublingual BHV-0223.

Study Design

Study BHV223-102 is a single center, Phase 1, bioequivalence, food-effect, open-label, single-dose study, designed to be conducted in three sequential parts:
  Part I: bioequivalence, randomized, open-label, fast, single-dose, 2-period, 2-sequence, crossover, design.
  Part II: food-effect, open-label, fed, single-dose, 1-period design.
  Part III: sublingual, open-label, fasting, single dose, 1-period design.

Selection of the subset of subjects who undergo Part II will be based on convenience (e.g., first 72 subjects who are able to commit to attending three dosing periods). Selection of subjects who undergo Part III will be also based on convenience (e.g., first 6 subjects available after completion of Part II).

The study is intended to dose in more than one group; all groups will be dosed at the same clinical site and the same protocol requirements and procedures will be followed within each group.

Study Population
Sample Size
  A total of 138 healthy adult male or female volunteers will be dosed.
  Seventy-two (72) subjects will undergo dosing under fed conditions in order to evaluate potential food effects. Considering an expected ratio within 0.87-1.15 and an intra-CV of 18% for AUC, an expected ratio within 0.95-1.05 and an intra-CV of 38% for $C_{max}$, n=60 (+12 subjects) would provide 80% power to show bioequivalence of BHV-0223 between the fed and fasted states.

Six (6) subjects who have undergone dosing in Part I and II will undergo dosing in Part III. The sample is empirically determined to provide qualitative data.

Inclusion Criteria

Subjects enrolled in this study will be members of the community at large.
1) Male or female, non-smoker (no use of tobacco products within 3 months prior to screening), 18 years of age and older, with BMI>18.5 and <30.0 kg/m2 and body weight ≥50.0 kg for males and ≥45.0 kg for females.
2) Healthy as defined by:
a) the absence of clinically significant illness and surgery within 4 weeks prior to dosing. Subjects vomiting within 24 hours pre-dose will be carefully evaluated for upcoming illness/disease. Inclusion pre-dosing is at the discretion of the Qualified Investigator.
b) the absence of clinically significant history of neurological, endocrinal, cardiovascular, pulmonary, hematological (e.g. neutropenia), immunologic, psychiatric, gastrointestinal, renal, hepatic, and metabolic disease.

Clinical Procedures

Unless otherwise specified, procedures, data collection and evaluation will be conducted as per inVentiv SOPs. Subjects' personal information will be stored in an electronic data capture system, Initiator™. Adverse events will be recorded electronically using Initiator™ or on raw data sheets (when electronic data capture is not possible). All laboratory results provided by Biron biomedical laboratory will be stored in InLab (Clinical Laboratory Information Management System). Initiator™ and InLab are validated and are Code of Federal Regulations (CFR) part 11 compliant applications. All other clinical data will be recorded on site by the clinical staff using Initiator™ or raw data sheets.

Screening Procedures

Subject screening procedures will be performed within 28 days preceding administration of study medication. Subjects must provide written informed consent prior to initiation of any screening procedures. The consent to perform some general screening procedures may be obtained on a consent document other than the Informed Consent Form (ICF) specific to this study, and therefore, some screening test results could be obtained before signature of the ICF specific to this study. The study-specific ICF must be signed and dated by the subject before participation to study-specific procedures.

Screening procedures will include: demographic data, medical and medication histories, physical examination, body measurements, ECG (12-lead), vital signs (blood pressure, heart rate, and respiratory rate), oral temperature, hematology, human immunodeficiency virus (HIV), hepatitis B (HBsAg) and hepatitis C (HCV) tests, biochemistry, urinalysis, urine cotinine test, urine pregnancy test, and urine drug screen.

For eligibility purposes, abnormal laboratory or vital signs results may be repeated once if abnormal result is observed at the initial reading. Moreover, abnormalities found in the ECG may need to be confirmed by repeated measurements. In the event that the participation of a subject in the study is delayed and some screening procedures had been performed outside the prescribed screening window, outdated screening procedures can be repeated.

Randomization and Blinding

In Part I, subjects will be administered each treatment according to the 2-period, 2-sequence, block randomization scheme produced by inVentiv. A subset of subjects will then undergo the Part II and III. The randomization code will not be available to the Bioanalytical Division of inVentiv until the clinical and analytical phases of the study have been completed.

Study Medication

Treatment A (Test-fasting): Riluzole 40 mg sublingual (SL), orally disintegrating tablet (BHV-0223, Biohaven Pharmaceutical Holding Company Limited, USA) administered as 1×40 mg BHV-0223 ODT to be held under the tongue for approximately 120 seconds without swallowing, administered under fasting conditions.

Treatment B (Reference-fasting): Riluzole 50 mg tablet (Rilutek®, Covis Pharmaceuticals, Inc.) 1×50 mg tablet swallowed with water, administered under fasting conditions.

Treatment C (Test-fed): Riluzole 40 mg sublingual (SL), orally disintegrating tablet (BHV-0223, Biohaven Pharmaceutical Holding Company Limited, USA) administered as 1×40 mg BHV-0223 ODT to be held under the tongue for approximately 120 seconds without swallowing, administered under fed conditions Treatment D (Reference-fasting) Riluzole 50 mg tablet (Rilutek, Covis Pharmaceuticals, Inc.) administered as 1×50 mg tablet crushed and placed under the tongue for two minutes duration, followed by discarding (spitting) and rinsed out with three mouthfuls of water. No swallowing of material.

Drug Administration

Each subject will receive treatments A and B once, as per their randomized sequence (either Treatment A followed by Treatment B or Treatment B followed by Treatment A). Following that, a subset of subjects will undergo Treatment C, and then a subset of subjects will undergo Treatment D.

For Treatments A and C (BHV-0223 ODT), subjects will be required not to wear dentures, braces or piercings at the time of dosing. Subjects will be allowed to rinse their mouth with approximately 20 ml of water immediately prior to dosing. The BHV-0223 ODT will be placed under the subject's tongue immediately after removal from the blister unit. Subjects will be instructed to hold the sublingual tablet under the tongue for approximately 120 seconds without swallowing and not to crush or chew it. Any inadvertent swallows within the 120 seconds should be recorded. Upon completion of the 120 seconds, the presence or absence of solid material under the tongue or in the mouth and any signs of irritation will be recorded in the source data and reported in the CRF. Then, a glass of water (240 mL) will be consumed by the subject to ensure ingestion of all study medication. Time of dosing will be set to the time the tablet is placed under the subject's tongue. If the tablet is not dissolved within 2 minutes (i.e. before swallowing the glass of water), it will be swallowed with water and this will be documented.

For treatment B, study medication will be administered to each subject with 240 ml of water and a hand and mouth check will be performed to ensure consumption of the medication.

For treatment D, subjects will be required not to wear dentures, braces or piercings at the time of dosing. One crushed tablet will be placed under the tongue for 120 seconds without swallowing and not to crush or chew it. The remaining of the crushed tablet will then be discarded (spitted) and rinsed out with three mouthfuls of water. No material must be swallowed.

Sample Collection and Processing
Blood Samples

In each period, a total of 19 blood samples will be drawn from each subject for pharmacokinetic analyses. Blood samples will be collected prior to drug administration and 0.083, 0.167, 0.333, 0.5, 0.667, 0.833, 1, 1.5, 2, 2.5, 3, 4, 6, 8, 12, 16, 24, and 48 hours post-dose (6 mL for each sampling time). For the 48-hour post-dose timepoint, a window of ±30 minutes will be allowed for blood collection. Actual post-dose sampling times will be used for statistical analyses. Unless otherwise specified or for subject safety, when blood draws and other procedures coincide, blood draws will have precedence. A dead-volume intravenous catheter will be used for blood collection to avoid multiple skin punctures, when appropriate. Otherwise, blood samples will be collected by direct venipuncture.

For subjects that will undergo the two first periods, the total volume of blood including that collected for eligibility and safety purposes should not exceed 290 ml for the whole study.

For subjects that will undergo the third period, the total volume of blood should not exceed 412 ml, for the whole study.

For subjects that will undergo the fourth period, the total volume of blood should not exceed 534 ml, for the whole study.

Plasma samples will be collected and processed as per the Analytical Methodology Information Sheet.

Urine Samples

In Part 1 only, and for 12 subjects, urine samples will be collected for quantitation of riluzole and its metabolites at the following time intervals: spot pre-dose (within 15 minutes before dosing), 0-4, 4-8, and 8-12 hour post-dose.

If a subject cannot void his bladder within 15 minutes before dosing, a sample from earlier that morning may be used as the pre-dose sample. Voids that occur within the time interval will be pooled, and subjects will be asked to void their bladder within 10 minutes before the end of each collection interval, so that each new interval will begin with an empty bladder. Any urine voided by subjects at the intersection (within 10 minutes) of two intervals will be included in the earlier sample. Any urine voided by subjects but not collected will be documented.

Data Collection and Evaluation

All clinical raw data will be recorded promptly, accurately, and legibly; either directly into the Initiator™ CTMS system as e-source data or indelibly on paper (e.g. ECG readings). A detailed list of the type (electronic or paper) and location for all source data will be included in the Trial Master File. When recorded electronically using Initiator™, Case Report Forms will be electronically generated afterwards. All raw data will be conserved in order to maintain data integrity. A physician and/or the clinical staff will assume the responsibility of ensuring the completeness and accuracy of the clinical data.

Analytical Methodology

When applicable, samples will be transported to the bioanalytical facility in at least two separate shipments, with each set of aliquots in separate shipments. Once the bioanalytical laboratory confirms receipt of the first shipment, the second set of aliquots may be sent. The samples should be packed on sufficient dry ice to keep them frozen for at least 72 hours.

The Bioanalytical Division of inVentiv will analyze riluzole and its metabolites in plasma and urine samples using a validated LC/MS/MS method. The following metabolites will be analysed in plasma: riluzole/riluzolamide/N—OH-riluzole-O-glucuronide/Riluzolamide N-glucuronide.

Other metabolites in plasma and urine may be analyzed for exploratory evaluation if necessary.

Analyst and Watson LIMS (Laboratory Information Management System) will be used at different steps of the analysis.

Samples from subjects included in the pharmacokinetic population (see section 12.2.2) and from subjects who were withdrawn from the study due to adverse events, or vomiting episodes will be analyzed.

Pharmacokinetic, Safety, and Statistical Analyses

Pharmacokinetic analysis will be performed using Phoenix® WinNonlin®, which is validated for bioequivalence/bioavailability studies by inVentiv. Inferential statistical analyses will be performed using SAS® according to FDA guidelines.

Bioanalysis of all samples should be completed prior to the initiation of the pharmacokinetic and statistical analyses.

Pharmacokinetics

The following pharmacokinetic parameters will be calculated with plasma concentrations by standard non-compartmental methods for riluzole and its metabolites:
1) $AUC_{0-t}$: area under the concentration-time curve from time zero to the last non-zero concentration
2) $AUC_{0-inf}$: area under the concentration-time curve from time zero to infinity (extrapolated)
3) $C_{max}$: maximum observed concentration
1) Residual area: calculated as $100*(1-AUC_{0-t}/AUC_{0-inf})$
2) $T_{max}$: time of observed $C_{max}$
3) $T1/2_{el}$: elimination half-life
4) $K_{el}$: elimination rate constant Urine samples will be used to calculate the following parameters:
1) $Ae_{0-t}$: Cumulative urinary excretion from time zero to time t, calculated as the sum of the amounts excreted over each collection interval. The amount excreted in urine for each time interval is calculated as the urine concentration multiplied by the urine volume.
2) $R_{max}$: Maximum rate of urinary excretion, calculated by dividing the amount of drug excreted in each collection interval by the time over which it was collected.
3) $T_{max}$: Time of $R_{max}$, calculated as the midpoint of the collection interval during which $R_{max}$ occurred.
4) $Cl_R$: calculated as $Ae_{0-t}/AUC_{0-t}$ Additional pharmacokinetic analysis may be performed. Upon the Sponsor's request, pharmacokinetic repeats might be performed according to inVentiv's SOP. If re-assays are requested for pharmacokinetic reasons, final results will include re-assay values, while results with original values will be presented in an appendix of the report as supportive data.

Analysis Populations
Safety Population

The safety population is defined as all subjects who received at least one dose of the study medication.

Pharmacokinetic Population

The pharmacokinetic population will include all subjects completing at least 2 periods, including at least Treatment A, and for whom the pharmacokinetic profile can be adequately characterized.

Any subject with pre-dose concentrations will be excluded from the pharmacokinetic and statistical analysis for the concerned period if the pre-dose concentration is greater than 5% of the $C_{max}$ value of that period for that subject. Data from subjects who experienced emesis during the sampling interval and who were not withdrawn may be evaluated after completion of the pharmacokinetic analysis. Any subject who experienced emesis within 2 times median $T_{max}$ of the current study (based on the reference product) will be excluded from the statistical analysis. Data (concentrations and pharmacokinetic parameters) from subjects excluded due to a pre-dose concentration greater than 5% of their $C_{max}$ or from subjects withdrawn due to adverse events or vomiting episodes will be presented but excluded from descriptive statistics for the concerned period.

Safety and Tolerability Parameters and Analyses

The safety and tolerability of BHV-0223 will be assessed by monitoring AEs, clinical laboratory values, vital signs, concomitant medications, and overall well-being throughout the study.

Vital signs and clinical laboratory determinations will be summarized using actual values for each treatment. All data gathered will be listed by subject and parameter.

Demographic parameters will be summarized descriptively. Treatment-emergent AEs (TEAEs) will be summarized descriptively by treatment, relationship, and severity for all subjects who were dosed (safety population). The MedDRA dictionary will be used to code AEs by system organ class and preferred term. A listing of all TEAEs will be provided. No inferential statistical analysis of safety data is planned.

Concomitant medications will be listed. Results of urine drug screens, virology tests, clinical laboratory tests, alcohol breath tests, and urine cotinine tests will be listed. Local tolerability assessment results will also be listed.

A complete description of the statistical analyses to be performed on the safety and tolerability data will be presented in the Statistical Analysis Plan.

Statistical Analyses

Individual and mean plasma concentration versus time curves will be presented for both linear and semi-log scales. Descriptive statistics (arithmetic and geometric means, standard deviation [SD], coefficient of variation [CV %], minimum [Min], maximum [Max], and median) of the plasma concentrations versus time will be presented as well for the pharmacokinetic parameters.

For riluzole, using GLM procedures in SAS, ANOVA will be performed on untransformed $T_{max}$, $K_{el}$ and $T1/2_{el}$ and on ln-transformed $AUC_{0-t}$, $AUC_{0-inf}$ and $C_{max}$ at the alpha level of 0.05. Factors incorporated in the model will include: Sequence, Subject (Sequence), Period, and Treatment. If the study doses in more than one group, the statistical model will be modified to reflect the multigroup nature of the study. In the case of a non-statistically significant treatment-by-group interaction term, the analysis will be rerun excluding this term from the ANOVA model in order to obtain ratios and confidence intervals where appropriate. Intra and inter-subject coefficient of variation (ISCV %) will be estimated. The ratio of geometric means (A/B) and 90% confidence interval for the ratio of geometric means, based on least-squares means from the ANOVA of the ln-transformed data, will be calculated for $AUC_{0-t}$, $AUC_{0-inf}$ and $C_{max}$.

For riluzole, using GLM procedures in SAS, ANOVA will be performed on untransformed $T_{max}$, $K_{el}$ and $T1/2_{el}$ and on ln-transformed $AUC_{0-t}$, $AUC_{0-inf}$ and $C_{max}$ at the alpha level of 0.05. Factors incorporated in the model will include: Sequence, Subject (Sequence), Period, and Treatment. If the study doses in more than one group, the statistical model will be modified to reflect the multigroup nature of the study. In the case of a non-statistically significant treatment-by-group interaction term, the analysis will be rerun excluding this term from the ANOVA model in order to obtain ratios and confidence intervals where appropriate. Intra and inter-subject coefficient of variation (ISCV %) will be estimated. The ratio of geometric means (C/A) and 90% confidence interval for the ratio of geometric means, based on least-squares means from the ANOVA of the ln-transformed data, will be calculated for $AUC_{0-t}$, $AUC_{0-inf}$ and $C_{max}$.

For riluzole, using GLM procedures in SAS, ANOVA will be performed on untransformed $T_{max}$, $K_{el}$ and $T1/2_{el}$ and on ln-transformed $AUC_{0-t}$, $AUC_{0-inf}$ and $C_{max}$ at the alpha level of 0.05. Factors incorporated in the model will include: Sequence, Subject (Sequence), Period, and Treatment. If the study doses in more than one group, the statistical model will be modified to reflect the multigroup nature of the study. In the case of a non-statistically significant treatment-by-group interaction term, the analysis will be rerun excluding this term from the ANOVA model in order to obtain ratios and confidence intervals where appropriate. Intra and inter-subject coefficient of variation (ISCV %) will be estimated. The ratio of geometric means (D/B) and 90% confidence interval for the ratio of geometric means, based on least-squares means from the ANOVA of the ln-transformed data, will be calculated for $AUC_{0-t}$, $AUC_{0-inf}$ and $C_{max}$.

The analysis for each comparison will be conducted excluding the data from the treatment that is not relevant for the comparison in question. Whenever a PK parameter can be calculated for only one period for a subject, the subject will be excluded from the ANOVA involving this parameter. However, data from the available period will be included in the descriptive statistics.

Additional statistical analysis may be performed. More details will be provided in the SAP.

Summary statistics will be used to describe plasma metabolites and urinary excretion. Any results of these analyses will be reported outside of the BHV-0223-102 clinical study report.

Criteria for Average Bioequivalence for Riluzole

The 90% geometric confidence intervals of the ratio (A/B) of least-squares means from the ANOVA of the ln-transformed $AUC_{0-t}$, $AUC_{0-inf}$ and $C_{max}$ must be within 80.00% to 125.00% of values for RILUTEK.

Criteria for Determination of No Food-Effect

For BHV-0223, no food effect will be concluded if the 90% geometric confidence intervals of the ratio (C/A) of least-squares means from the ANOVA of the ln-transformed $AUC_{0-t}$, $AUC_{0-inf}$ and $C_{max}$ are within 80.00% to 125.00% of fasting PK values.

REFERENCES

1. RILUTEK, Prescribing Information. Version revised on 04/2016. Available online at: http://www.accessdata.fda.gov/drugsatfda_docs/label/2016/020599s017lbl.pdf
2. RILUTEK, Product Monograph. Version revised on May 11, 2010. Drug Product Database, Health Canada. Available online at: http://webprod5.hc-sc.gc.ca/dpd-bdpp/index-eng.jsp
3. Le Liboux, A., et al. Single- and Multiple-Dose Pharmacokinetics of Riluzole in White Subjects. J Clin Pharmacol. 1997. 37:820-827.
4. FDA Guidance on Riluzole. Finalized May 2008. Available online at: http://www.fda.gov/downloads/Drugs/GuidanceComplianceRegulatoryinformation/Guid ances/ucm089580.pdf

Example 2

Study Results from Example 1

The study (BHV223-102) as substantially described in protocol set forth in Example 1 was conducted. The results are summarized below.

Results: In Part I, BHV-0223 achieved area under the curve (AUC) and maximum concentration exposures of approximately 90% and 113%, respectively, compared to RILUTEK. The 90% confidence intervals were within the 80%-125% range required by FDA for bioequivalence. BHV-0223 generated AUC levels with a fed-to-fasted ratio of 92%. Crushed, sublingual RILUTEK delivered AUC levels with a ratio of 6%, compared to oral RILUTEK.

Summary/Conclusion: BHV-0223 is bioequivalent to, and thus offers similar efficacy as, RILUTEK 50 mg oral tablet; but also potentially increases usability and reduces burden on patients (no need to swallow and no negative food-effect requiring fasting based on AUC); improves safety/tolerability (lower risk of dose-related liver function abnormalities); and enhances the pharmacological profile (less PK variability).

The results are further set forth in Tables 1-4 below.

TABLE 1

Summary of Descriptive Statistics for PK Parameters for Riluzole (1 of 2)

| | | | Treatment | | | | | | |
|---|---|---|---|---|---|---|---|---|---|
| | | | 1 × 40 mg BHV-0223 ODT-Fast | | | | RILUTEK 1 × 50 mg tablet | | |
| Analyte | PK Parameter | N | Mean | SD | CV % | N | Mean | SD | CV % |
| Riluzole | $AUC_{0-t}$ | 134 | 647894.10 | 247608.02 | 38.22 | 134 | 741005.01 | 336139.96 | 45.36 |
| | $AUC_{0-inf}$ | 134 | 670485.92 | 258531.82 | 38.56 | 134 | 768319.54 | 355237.50 | 46.24 |
| | Residual area | 134 | 3.34 | 1.61 | 48.33 | 134 | 3.35 | 1.66 | 49.40 |
| | $C_{max}$ | 134 | 185487.88 | 83817.68 | 45.19 | 134 | 177441.43 | 104799.03 | 59.06 |
| | $T_{max}$ | 134 | 0.646 | 0.197 | 30.440 | 134 | 1.088 | 0.753 | 69.170 |
| | $T_{1/2\ el}$ | 134 | 10.99 | 2.07 | 18.82 | 134 | 10.99 | 1.98 | 17.98 |
| | $K_{el}$ | 134 | 0.0657 | 0.0148 | 22.5743 | 134 | 0.0654 | 0.0141 | 21.489 |
| N-hydroxy-riluzole | $AUC_{0-t}$ | 133 | 144634.46 | 44835.74 | 31.00 | 133 | 177495.41 | 61013.97 | 34.38 |
| | $AUC_{0-inf}$ | 132 | 153786.67 | 47699.66 | 31.02 | 133 | 187697.97 | 64598.23 | 34.42 |
| | Residual area | 132 | 5.95 | 2.34 | 39.42 | 133 | 5.39 | 1.99 | 36.98 |
| | $C_{max}$ | 133 | 68334.11 | 31115.74 | 45.53 | 133 | 70481.73 | 38301.15 | 54.34 |
| | $T_{max}$ | 133 | 0.593 | 0.182 | 30.661 | 133 | 0.891 | 0.671 | 75.312 |
| | $T_{1/2\ el}$ | 132 | 6.85 | 2.14 | 31.23 | 133 | 6.80 | 2.16 | 31.69 |
| | $K_{el}$ | 132 | 0.1112 | 0.0359 | 32.3047 | 133 | 0.1117 | 0.0352 | 31.5159 |

| | | | Treatment | | | | | | |
|---|---|---|---|---|---|---|---|---|---|
| | | | 1 × 40 mg BHV-0223 ODT-Fed | | | | RILUTEK 1 × 50 mg tablet crushed | | |
| Analyte | PK Parameter | N | Mean | SD | CV % | N | Mean | SD | CV % |
| Riluzole | $AUC_{0-t}$ | 67 | 572333.18 | 208840.31 | 36.49 | 6 | 70412.84 | 115733.43 | 164.36 |
| | $AUC_{0-inf}$ | 67 | 598736.24 | 225502.60 | 37.66 | 6 | 78454.64 | 122322.87 | 155.92 |
| | Residual area | 67 | 4.24 | 2.29 | 53.98 | 6 | 17.75 | 12.17 | 68.56 |
| | $C_{max}$ | 67 | 68112.73 | 26335.23 | 38.66 | 6 | 20502.87 | 24593.42 | 119.95 |
| | $T_{max}$ | 67 | 2.274 | 1.622 | 71.356 | 6 | 0.528 | 0.245 | 46.513 |
| | $T_{1/2\ el}$ | 67 | 10.93 | 2.12 | 19.36 | 6 | 7.23 | 4.11 | 56.91 |
| | $K_{el}$ | 67 | 0.0662 | 0.0155 | 23.4183 | 6 | 0.1272 | 0.079 | 62.1402 |
| N-hydroxy-riluzole | $AUC_{0-t}$ | 67 | 141600.26 | 39538.50 | 27.9226 | 6 | 8517.21 | 18248.43 | 214.25 |
| | $AUC_{0-inf}$ | 67 | 151587.69 | 42356.07 | 27.9416 | 4 | 14465.56 | 24110.23 | 166.67 |
| | Residual area | 67 | 6.55 | 2.25 | 34.3154 | 4 | 26.25 | 11.14 | 42.46 |
| | $C_{max}$ | 67 | 24590.85 | 13723.73 | 55.8083 | 6 | 3818.88 | 6538.94 | 171.23 |
| | $T_{max}$ | 67 | 1.881 | 1.461 | 77.706 | 5 | 0.633 | 0.139 | 22.003 |
| | $T_{1/2\ el}$ | 67 | 6.55 | 2.11 | 32.1449 | 4 | 2.06 | 2.27 | 110.18 |
| | $K_{el}$ | 67 | 0.1144 | 0.0305 | 26.6709 | 4 | 0.6153 | 0.3643 | 59.2045 |

TABLE 2

Ratio (A/B), 90% Geometric Confidence Intervals, Intra- and Inter-Subject CV %*

| | | | 90% Geometric C.I.[2] | | Intra-Subject CV | Inter-Subject CV |
|---|---|---|---|---|---|---|
| Parameter | Treatment Comparisons | Ratio[1] | Lower | Upper | CV | CV |
| $AUC_{0-t}$ | 1 × 40 mg BHV-0223 ODT-Fast (A)-RILUTEK 1 × 50 mg tablet (B) | 89.85% | 87.30% | 92.47% | 13.35% | 40.26% |
| $AUC_{0-inf}$ | 1 × 40 mg BHV-0223 ODT-Fast (A)-RILUTEK 1 × 50 mg tablet (B) | 89.83% | 87.32% | 92.41% | 13.13% | 40.51% |

TABLE 2-continued

Ratio (A/B), 90% Geometric Confidence Intervals, Intra- and Inter-Subject CV %*

| Parameter | Treatment Comparisons | Ratio[1] | 90% Geometric C.I.[2] | | Intra-Subject CV | Inter-Subject CV |
|---|---|---|---|---|---|---|
| | | | Lower | Upper | | |
| $C_{max}$ | 1 × 40 mg BHV-0223 ODT-Fast (A)- RILUTEK 1 × 50 mg tablet (B) | 112.72% | 105.53% | 120.40% | 31.18% | 39.95% |

[1]Calculated using least-squares means according to the formula: $e^{(A-B)} \times 100$.
[2]90% Geometric Confidence Interval using ln-transformed data.
*The treatment*group interaction term was found to be statistically significant for $AUC_{0-t}$, $AUC_{0-inf}$ and $C_{max}$ (p-values <0.05). Therefore, the ratio (A/B) and 90% CI were derived from the analysis with the treatment*group term.

TABLE 3

Ratio (C/A), 90% Geometric Confidence Intervals, Intra- and Inter-Subject CV %

| Parameter | Treatment Comparisons | Ratio[1] | 90% Geometric C.I.[2] | | Intra-Subject CV | Inter-Subject CV |
|---|---|---|---|---|---|---|
| | | | Lower | Upper | | |
| $AUC_{0-t}$ | 1 × 40 mg BHV-0223 ODT-Fed (C)- 1 × 40 mg BHV-0223 ODT-Fast (A) | 91.16% | 88.12% | 94.30% | 11.79% | 37.03% |
| $AUC_{0-inf}$ | 1 × 40 mg BHV-0223 ODT-Fed (C)- 1 × 40 mg BHV-0223 ODT-Fast (A) | 91.99% | 89.00% | 95.05% | 11.51% | 36.96% |
| $C_{max}$ | 1 × 40 mg BHV-0223 ODT-Fed (C)- 1 × 40 mg BHV-0223 ODT-Fast (A) | 38.85% | 36.26% | 41.61% | 24.23% | 34.16% |

[1]Calculated using least-squares means according to the formula: $e^{(C-A)} \times 100$.
[2]90% Geometric Confidence Interval using ln-transformed data.

TABLE 4

Ratio (D/B), 90% Geometric Confidence Intervals, Intra- and Inter-Subject CV %

| Parameter | Treatment Comparisons | Ratio[1] | 90% Geometric C.I.[2] | | Intra-Subject CV | Inter-Subject CV |
|---|---|---|---|---|---|---|
| | | | Lower | Upper | | |
| $AUC_{0-t}$ | RILUTEK 1 × 50 mg tablet crushed(D)- RILUTEK 1 × 50 mg tablet (B) | 4.74% | 2.24% | 10.00% | 71.51% | 68.06% |
| $AUC_{0-inf}$ | RILUTEK 1 × 50 mg tablet crushed(D)- RILUTEK 1 × 50 mg tablet (B) | 5.60% | 2.94% | 10.64% | 59.72% | 68.02% |
| $C_{max}$ | RILUTEK 1 × 50 mg tablet crushed(D)- RILUTEK 1 × 50 mg tablet (B) | 10.08% | 4.16% | 24.45% | 88.66% | 8.63% |

[1]Calculated using least-squares means according to the formula: $e^{(D-B)} \times 100$.
[2]90% Geometric Confidence Interval using ln-transformed data.

A further summary and description of the study and the results follows.

Objectives
Primary
   Compare the rate and extent of absorption of sublingual 40 mg BHV-0223 vs 50 mg Rilutek® oral tablets in healthy volunteers.
   Evaluate the effect of food on the PK of BHV-0223.
Secondary and Exploratory
   Assess safety and tolerability of BHV-0223.
   Assess rate of sublingual absorption of crushed 50 mg Rilutek tablets.
Methods
Subjects
   Subjects aged ≥18 years with no tobacco use in the 3 months prior to screening, body mass index (BMI) >18.5 and ≤30 kg/m2, body weight >50 kg for males and >45 kg for females, and able to provide informed consent were eligible for inclusion.
   Subjects with the presence of dentures, braces, or piercings at the time of dosing or a clinically significant medical history were excluded.
   Target enrollment was 138 subjects.
Study Design and Treatments
Part 1: Bioequivalence of BHV-0223 to Rilutek
   Open-label, single-dose, 2-period, 2-sequence, randomized crossover design.
   Subjects received a single 40 mg sublingual dose of BHV-0223 and a single 50 mg oral dose of Rilutek with 240 ml water, both under fasted conditions (no food from ≥10 hours before and ≥4 hours after dosing).
   138 subjects randomized equally into 1 of 2 treatment sequences (A→B or B→A).
   Washout period of 4 days between treatments.
Part 2: Food Effect on BHV-0223
   Open-label, single-dose, 1-period design.
   Subjects received a single 40 mg sublingual dose of BHV-0223 under fed conditions.
   After a supervised fast of ≥10 hours, subjects were served a high-fat, high-caloric meal of approximately 800-

1000 calories (approximately 50% total caloric content derived from fat). 72 subjects selected from subjects completing part 1 based on convenience.

Figure 7:
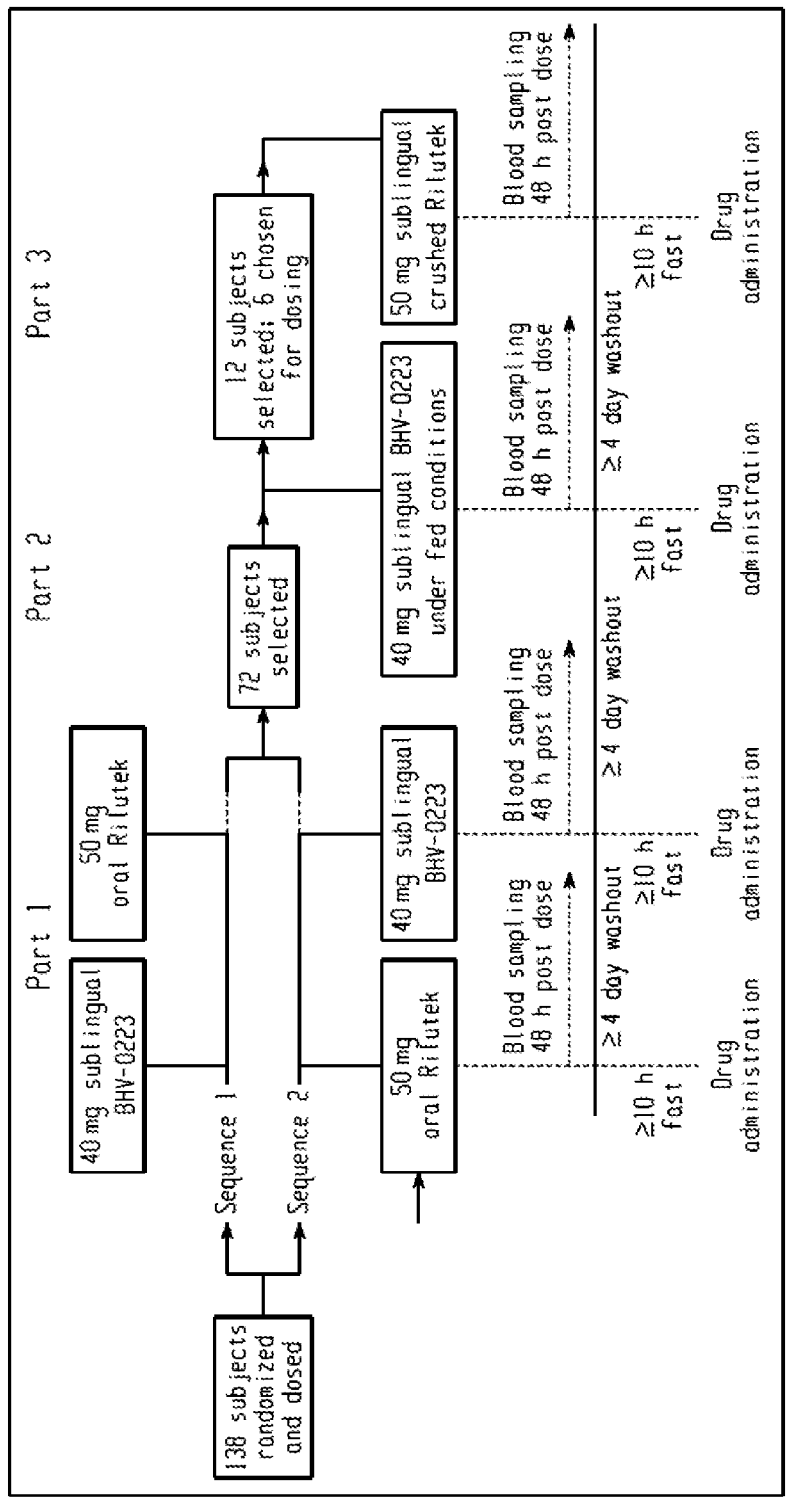
FIG. 7 is a schematic diagram showing clinical study design.

Part 3: Absorption of Sublingually Administered Crushed Rilutek Tablet
  Open-label, single-dose, 1-period design.
  Subjects received a single 50 mg sublingual crushed Rilutek tablet under fasted conditions.
  6 subjects selected from subjects completing part 2 based on convenience.
  Overall study design is shown in Schematic 1.
  The study design is schematically presented in FIG. 7.

PK and Safety Assessments
  Blood samples were drawn prior to and after drug administration for quantitation of riluzole and its metabolites.
  Primary PK endpoints were area under the concentration-time curve (AUC) from time zero to last non-zero concentration ($AUC_{0-t}$), AUC from time zero to infinity ($AUC_{0-\infty}$; extrapolated), and maximum observed concentration ($C_{max}$).
  Secondary PK endpoints were residual area, time of observed $C_{max}$, elimination half-life ($T_{1/2\ el}$), and elimination rate constant ($K_{el}$).
  Urine samples were collected from 12 subjects in part 1 only for quantitation of riluzole and its metabolites.
  Urine concentrations were used to calculate cumulative urinary excretion ($Ae_{0-t}$), maximum rate of urinary excretion ($R_{max}$), time of $R_{max}$, and renal clearance ($Cl_R$).
  Safety was evaluated based on adverse events (AEs), clinical laboratory investigations, vital signs, electrocardiograms, physical examinations, and oral safety and tolerability measurements.

Bioequivalence Criteria (as Defined by the FDA)
  For 40 mg sublingual BHV-0223 and 50 mg oral Rilutek to be considered bioequivalent, the 90% geometric confidence interval (CI) of the ratio of least squares (LS) means from the analysis of variance (ANOVA) for each treatment had to be within 80-125% of Rilutek, as per FDA-recommended bioequivalence criteria.

Results

Subjects
  287 subjects underwent screening, of whom 160 were enrolled, and 137 received ≥1 dose of BHV-0223 (FIG. 2).
  133 subjects completed both treatments in part 1 (bioequivalence).
  67 subjects were included in and completed part 2 (food effect).
  6 subjects completed part 3.
  2 subjects withdrew due to AEs (n=1 blood creatine phosphokinase increased and n=1 rash), 1 due to non-compliance with study drug, and 3 due to dosing irregularities.
  Subject demographics are shown in Table 5.

Figure 8:
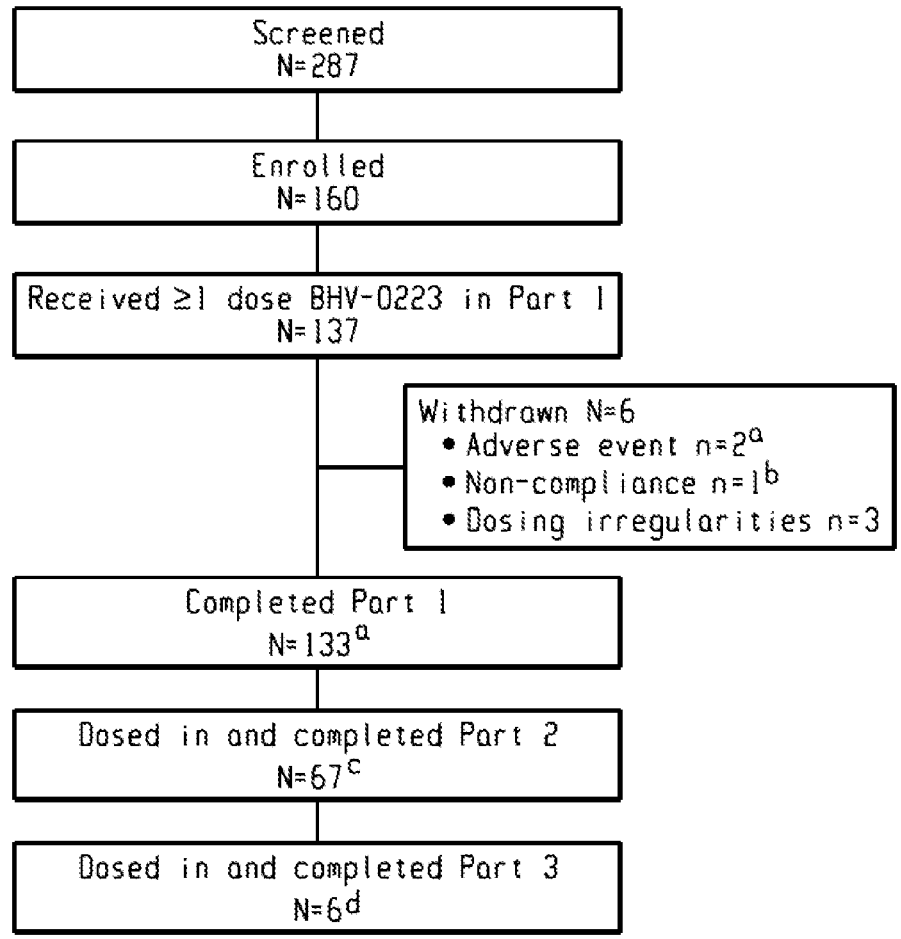
FIG. 8 is a schematic diagram showing disposition of subjects in the clinical study.

PK Analyses
  Plasma concentrations over time (FIG. 1) and other PK parameters (Table 6) were generally similar for fasted sublingual BHV-0223 and fasted oral Rilutek.
  The disposition of subjects is schematically presented in FIG. 8.

TABLE 5

| | | | |
|---|---|---|---|
| | \multicolumn{3}{c}{Subject demographics} | | |
| Characteristic | Part 1 Bioequivalence (N = 138) | Part 2 Food effect (N = 67) | Part 3 Crushed Rilutek (N = 6) |
| Age, mean (SD), years | 42.0 (13.0) | 45.6 (12.8) | 52.5 (10.2) |
| 18-40, n (%) | 68 (49) | 27 (40) | 1 (17) |
| >40, n (%) | 70 (51) | 40 (60) | 5 (83) |
| Male, n (%) | 69 (50) | 24 (36) | 4 (67) |
| Race, n (%) | | | |
| White | 134 (97) | 65 (97) | 6 (100) |
| Black | 2 (1) | 0 | 0 |
| Asian | 2 (1) | 2 (3) | 0 |
| Ethnicity, n (%) | | | |
| Not Hispanic or Latino | 111 (80) | 52 (78) | 5 (83) |
| Hispanic or Latino | 27 (20) | 15 (22) | 1 (17) |
| Height, mean (SD), cm | 167.2 (8.4) | 168.1 (8.7) | 167.0 (12.6) |
| Weight, mean (SD), kg | 70.6 (11.0) | 72.5 (9.5) | 72.5 (10.5) |
| BMI, mean (SD), kg/m² | 25.2 (2.7) | 25.6 (2.4) | 25.9 (1.6) | n = number of patients.
BMI, body mass index;
SD, standard deviation.

TABLE 6

PK parameters for BHV-0223 and Rilutek

| Parameter | Part 1 Fasted conditions 40 mg sublingual BHV-0223 (n = 133) | 50 mg oral Rilutek, with water (n = 132) | Part 2: Fed conditions 40 mg sublingual BHV-0223 (N = 67) | Part 3: Fasted conditions 50 mg sublingual crushed Rilutek, (N = 6) |
|---|---|---|---|---|
| $AUC_{0-t}$, mean ± SD, h·ng/mL (CV %) | 647.51 ± 248.68 (38) | 740.94 ± 338.45 (46) | 572.40 ± 208.95 (37) | 70.43 ± 115.84 (164) |
| $AUC_{0-\infty}$, mean ± SD, h·ng/mL (CV %) | 670.13 ± 259.66 (39) | 768.15 ± 357.63 (47) | 598.77 ± 225.56 (38) | 78.48 ± 122.42 (156) |
| Residual area, mean ± SD, % (CV %) | 3.34 ± 1.62 (48) | 3.34 ± 1.66 (50) | 4.24 ± 2.29 (54) | 17.77 ± 12.19 (69) |
| $C_{max}$, mean ± SD, ng/mL (CV %) | 185.01 ± 83.95 (45) | 177.58 ± 105.43 (59) | 68.11 ± 26.34 (39) | 20.50 ± 24.59 (120) |
| $T_{max}$, median (min, max), h | 0.66 (0.33, 1.50) | 0.83 (0.33, 4.00) | 2.50 (0.33, 8.01) | 0.50 (0.34, 1.00) |

TABLE 6-continued

PK parameters for BHV-0223 and Rilutek

| Parameter | Part 1<br>Fasted conditions<br>40 mg sublingual<br>BHV-0223<br>(n = 133) | 50 mg oral Rilutek<br>with water<br>(n = 132) | Part 2: Fed<br>conditions<br>40 mg sublingual<br>BHV-0223<br>(N = 67) | Part 3: Fasted<br>conditions<br>50 mg sublingual<br>crushed Rilutek,<br>(N = 6) |
|---|---|---|---|---|
| $T_{1/2\ el}$, mean ± SD, h (CV %) | 10.98 ± 2.08 (19) | 10.96 ± 1.97 (18) | 10.92 ± 2.11 (19) | 7.23 ± 4.11 (57) |
| $K_{el}$, mean ± SD, /h (CV %) | 0.07 ± 0.01 (23) | 0.07 ± 0.01 (21) | 0.07 ± 0.02 (23) | 0.13 ± 0.08 (62) |
| $K_{el}$ correlation coefficient, mean ± SD | −0.99 ± 0.01 | −0.99 ± 0.01 | −0.99 ± 0.01 | −0.95 ± 0.06 |

AUC, area under the concentration-time curve;
$AUC_{0-t}$, AUC from time zero to last non-zero concentration;
$AUC_{0-\infty}$, AUC from time zero to infinity;
$C_{max}$, maximum observed concentration;
CV, coefficient of variation;
$K_{el}$, the elimination rate constant;
SD, standard deviation;
$T_{1/2\ el}$, elimination half-life;
$T_{max}$, time to maximum concentration.

In part 1, sublingual BHV-0223 demonstrated bioequivalence to the Rilutek oral tablet formulation, with the geometric least squares (LS) mean ratios and derived geometric 90% CIs for $AUC_{0-t}$, $AUC_{0-\infty}$, and $C_{max}$ all within the predetermined acceptance range of 80-125% (Table 7).

TABLE 7

Geometric LS mean ratios and 90% CIs for $AUC_{0-t}$, $AUC_{0-\infty}$, and $C_{max}$

| Parameter | Sublingual BHV-0223 Rilutek (N = 132) | Sublingual BHV-0223 fed vs fasted (N = 67) | Rilutek crushed vs vs oral swallowed with water (N = 6) |
|---|---|---|---|
| $AUC_{0-t}$ | 90% (87-92) | 91% (88-94) | 5% (2-10) |
| $AUC_{0-\infty}$ | 90% (87-92) | 92% (89-95) | 6% (3-11) |
| $C_{max}$ | 113% (106-120) | 39% (36-42) | 10% (4-24) |

AUC, area under the concentration-time curve;
$AUC_{0-t}$, AUC from time zero to last non-zero concentration;
$AUC_{0-\infty}$, AUC from time zero to infinity;
$C_{max}$, maximum observed concentration;
CI, confidence interval;
LS, least squares.

Figure 2:
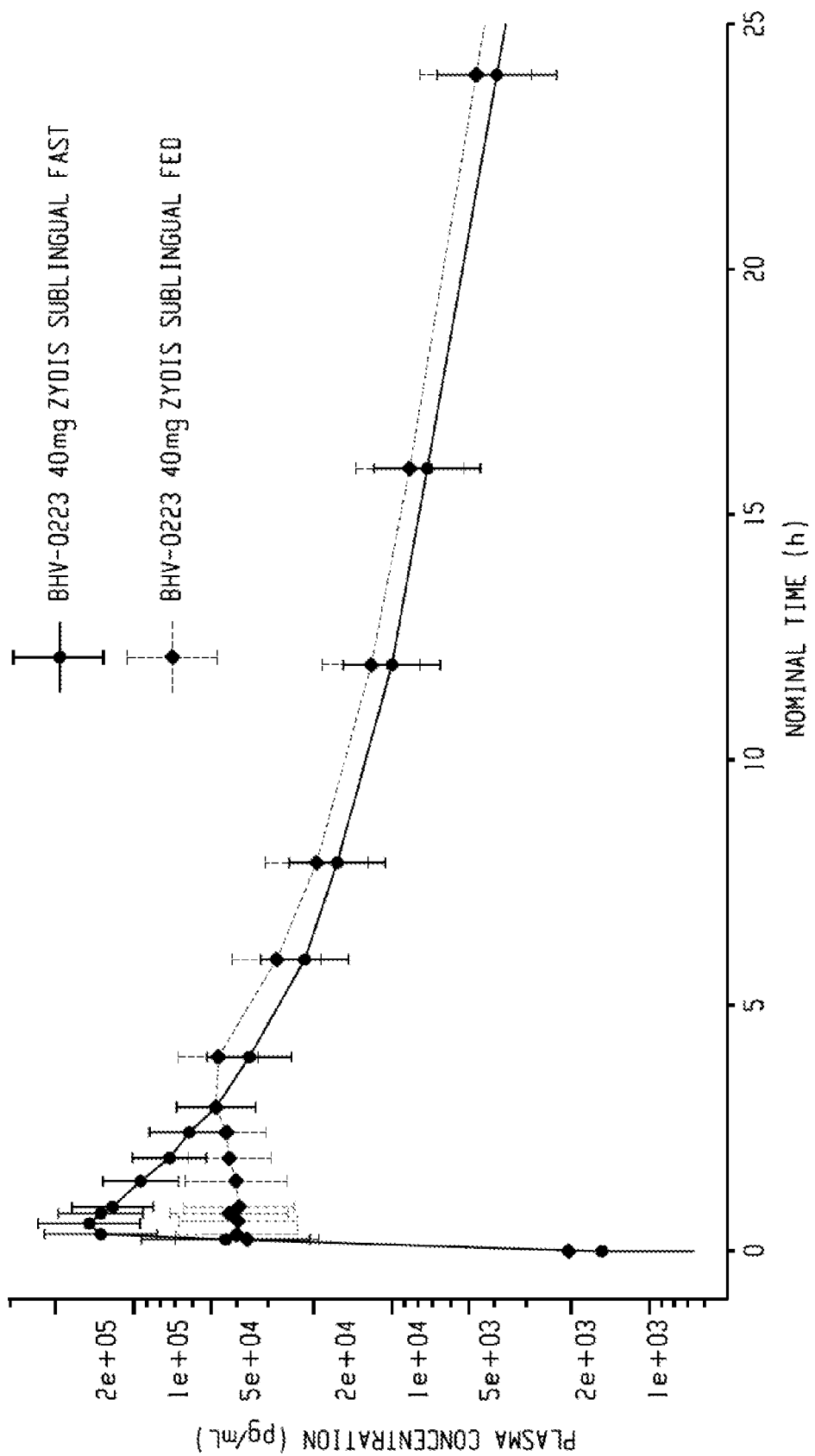
FIG. 2 illustrates riluzole plasma concentrations over time for BHV-0223 under fed and fasted conditions.

Plasma riluzole concentrations for fed vs fasted BHV-0223 for subjects included in part 2 are shown in FIG. 2. PK parameters for BHV-0223 are shown in Table 7. LS mean ratios and 90% CIs for $AUC_{0-t}$ and $AUC_{0-\infty}$ were within the predetermined range for rejection of a food effect, but $C_{max}$ was reduced by 61% and occurred approximately 1.8 hours later under fed conditions (Tables 6 and 7). AUC exposure levels, rather than $C_{max}$, are thought to drive the efficacy of riluzole in ALS, and thus a diminished $C_{max}$ is not expected to have any clinically meaningful impact on efficacy.

Mean residual area was <5% for parts 1 and 2 (Table 6), indicating that sampling over 48 hours was sufficient for riluzole.

Figure 3:
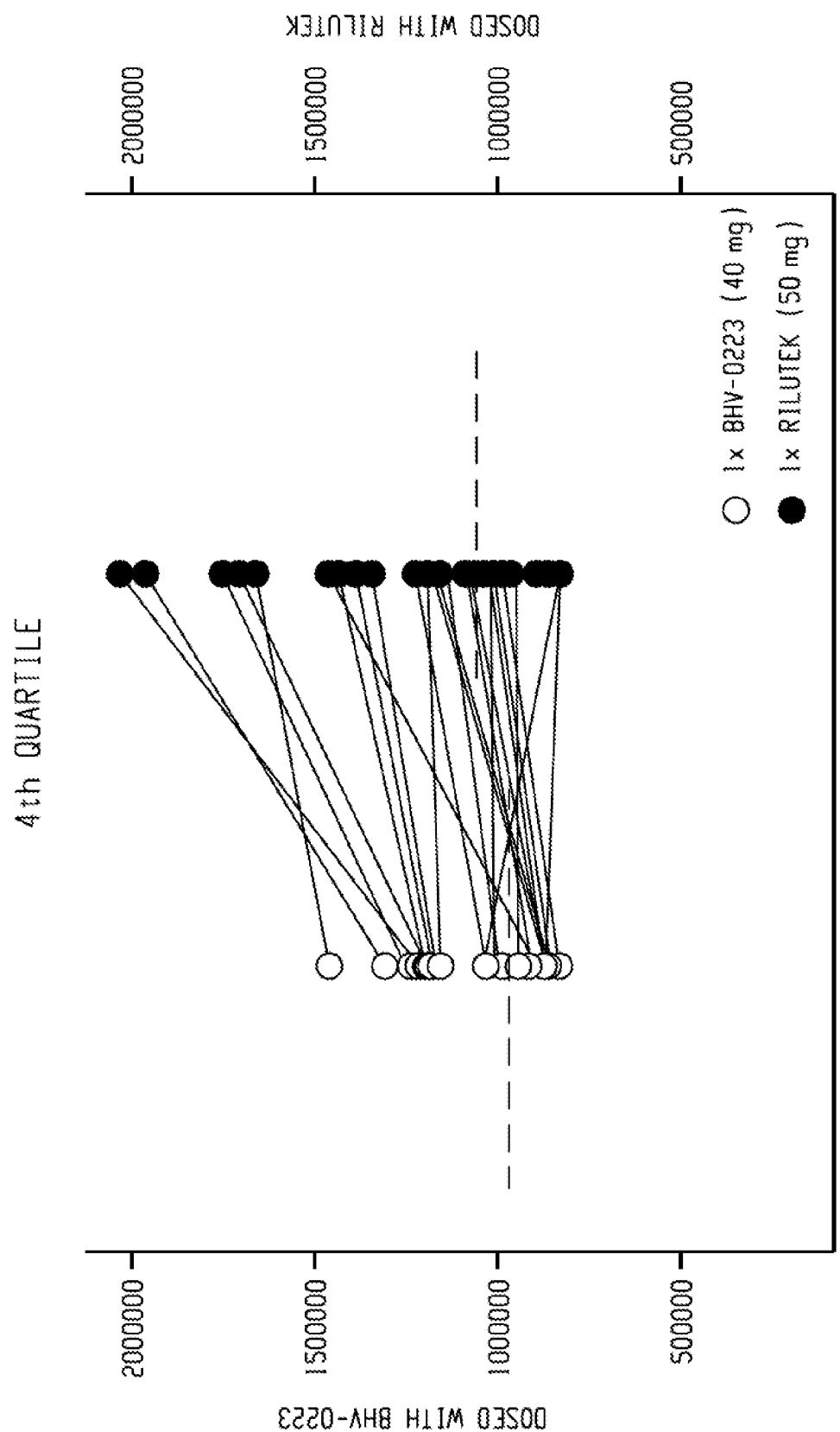
FIG. 3 illustrates the AUC, area under the concentration-time curve for BHV-0223 and Rilutek.

CVs observed for BHV-0223 PK parameters ($AUC_{0-t}$, $AUC_{0-\infty}$ and $C_{max}$) under both fed and fasted conditions were all lower than those observed for oral fasted Rilutek (Table 6, FIG. 3), indicating that PK variability was lower for BHV-0223 compared to oral Rilutek. In FIG. 3, the AUC, area under the concentration-time curve; $AUC_{last}$, AUC from time zero to time of last measurable concentration is shown and the dotted lines represent medians.

Sublingually administered 50 mg crushed Rilutek tablet had a lower rate and extent of absorption compared to 50 mg Rilutek tablet swallowed with water (Table 6), and mean ratios and 90% geometric CIs for $AUC_{0-t}$, $AUC_{0-\infty}$, and $C_{max}$ for this comparison were all <25% (Table 7).

Safety 126 of 138 subjects who received ≥1 dose of study drug reported a total of 253 AEs.

220 of 253 AEs (87%) were possibly or probably related to study medication and almost all (244 [96%]) were of mild severity.

A greater proportion of subjects had AEs after BHV-0223 (fed and fasted) than oral Rilutek (Table 8), primarily due to the incidence of oral hypoesthesia associated with BHV-0223.

No subjects experienced oral hypoesthesia after oral Rilutek swallowed with water.

All subjects who received crushed Rilutek tablets in part 3 also experienced oral hypoesthesia.

All cases of oral hypoesthesia (n=116 [84%]) were deemed possibly related to study drug.

Median (range) time to resolution was 34 (1-91) min.

Other frequently reported AEs were headache and dysphagia (Table 8).

AEs of headache were mostly mild and transient.

AEs of dysphagia were all mild and transient with median (range) time to resolution of 30 (1-58) min, and were not associated with functional changes (e.g., no reports of choking, coughing, aspiration, etc).

No serious AEs or deaths on study were reported.

TABLE 8

Summary of adverse events

| | Fasted 40 mg sublingual BHV-0223 (n = 137) | 50 mg oral Rilutek with water (n = 138) | Fed 40 mg sublingual BHV-0223 (N = 67) | 50 mg oral Rilutek, crushed (N = 6) | Overall (N = 138) |
|---|---|---|---|---|---|
| Number of AEs | 157 | 26 | 63 | 7 | 253 |
| Mild | 153 | 24 | 60 | 7 | 244 |
| Moderate | 4 | 2 | 3 | 0 | 9 |
| Number of related AEs | 144 | 16 | 53 | 7 | 220 |
| Subjects with ≥1 AE, n (%) | 118 (86) | 23 (17) | 45 (67) | 6 (100) | 126 (91) |
| Oral hypoaesthesia | 111 (81) | 0 | 40 (60) | 6 (100) | 116 (84) |
| Dysphagia | 9 (7) | 0 | 6 (9) | 0 | 14 (10) |
| Headache | 6 (4) | 7 (5) | 4 (6) | 1 (17) | 14 (10) |
| Discontinuations due to AEs, n | 1 | 1 | 0 | 0 | 2 | n = number of patients.
AE, adverse event.

No clinically meaningful changes in laboratory values, vital signs, physical measurements, or electrocardiograms were observed.

Oral assessment and local tolerability indicated no clinically important lasting effects of BHV-0223.

Conclusions

The BHV-0223 40 mg sublingual Zydis formulation of riluzole offered similar efficacy to the Rilutek 50 mg oral tablet formulation, by virtue of being bioequivalent.

BHV-0223 was not subject to a clinically meaningful food effect.

BHV-0223 had an enhanced pharmacological profile, exhibiting less PK variability than Rilutek.

No novel safety concerns were observed with BHV-0223.

BHV-0223 potentially offered increased usability and reduced burden on patients compared to Rilutek tablets.

Example 3

Simulations and Modelling

Part A
Assessing Effects of BHV-0223 40 Mg Zydis® Sublingual Formulation and Riluzole 50 Mg Oral Tablet on Liver Function Test Parameters Utilizing Dilisym® Modelling Software The primary elements of the simulation are summarized as follows.

Objective

To quantitatively and mechanistically compare the liver toxicity potential of oralriluzole versus BHV-0223, combining clinical and mechanistic data, using DILIsym. DILIsym is a registered trademark of Dilisym Services Inc., Durham, NC, USA.

Methods

Oral riluzole (50 mg twice daily [BID] for 12 weeks) and sublingual riluzole (40 mg BID for 12 weeks) were simulated by combining a physiologically based pharmacokinetic (PBPK) modelling representation of riluzole with mechanistic liver toxicity parameters derived from in vitro data.

The DILIsym PBPK model framework used for riluzole consists of a compartmental model of the body with compartments for blood, gut, liver, muscle, and other tissues.

The PBPK representation of riluzole was based on available data for BHV-0223 and published studies of riluzole.

Data on plasma riluzole exposure from a published pharmacokinetics (PK) study of riluzole (single 50 mg intravenous [IV] dose and single 100 mg oral dose in healthy volunteers) were used to optimize the model parameters.

The model was validated against clinical data from a completed phase 1 trial and previously published trials in healthy volunteers, including the PK study of ascending doses of riluzole (25, 50, or 100 mg dose BID).

PK data were used to estimate the portion of sublingual riluzole that is absorbed via the oral mucosa and the portion that is swallowed and passes through the gastrointestinal (GI) tract.

Simulated plasma concentrations after a 35 mg sublingual dose were conducted, assuming variable amounts absorbed via the oral mucosa.

Simulations were conducted in DILIsym SimPops and SimCohorts to assess the hepatotoxic potential of oral and sublingual riluzole.

SimPops are collections of simulated individuals with parameter variability designed to reflect appropriate biochemical and anthropometric ranges.

SimCohorts are relatively small groups of simulated individuals consisting of a subset of individuals from existing SimPops generated for screening and sensitivity analysis purposes.

For this study, a SimPops (N=285) with variability in mitochondrial function, caspase activation (apoptosis), bile acid concentrations, and oxidative stress was utilized.

The SimCohorts utilized for this study included the baseline human and 13 sensitive individuals and 2 individuals with low sensitivity in the areas of oxidative stress, mitochondrial dysfunction, bile acid transport inhibition, and combined bile acid transport inhibition and mitochondrial dysfunction.

Simulations were performed with median and high PK parameterizations (representing median and high plasma riluzole exposure) combined with default and high riluzole liver-to-blood partition coefficients (liver $K_b$).

PK parameterizations were based on variability observed in the completed

BHV-0223 phase 1 study and were consistent with exposures 1 standard deviation above the median level.

$K_b$ values were based on available in vitro data and in silico calculations; the high $K_b$ value represented the highest value calculated from in vitro data.

Results

PBPK Optimization

Figure 4B:
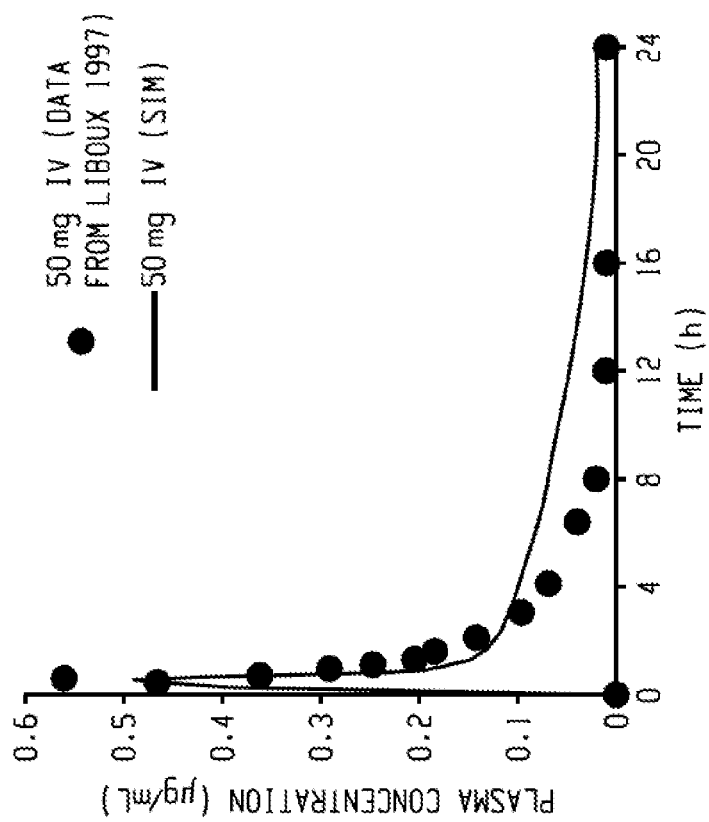
FIG. 4 illustrates simulated and observed plasma concentrations of riluzole following a single 100 mg oral dose and a single 50 mg IV dose.
Figure 4A:
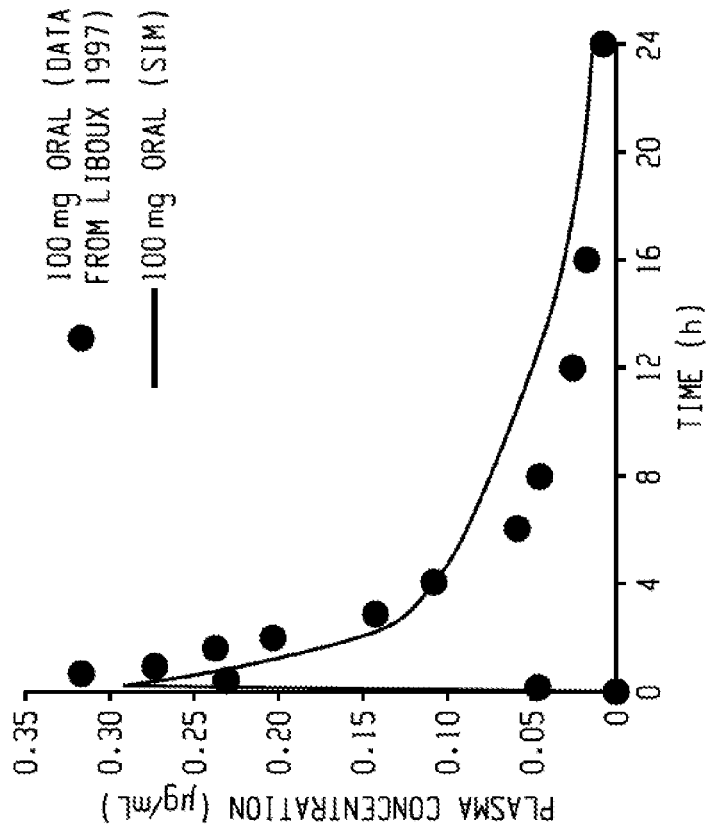
Figure 5A:
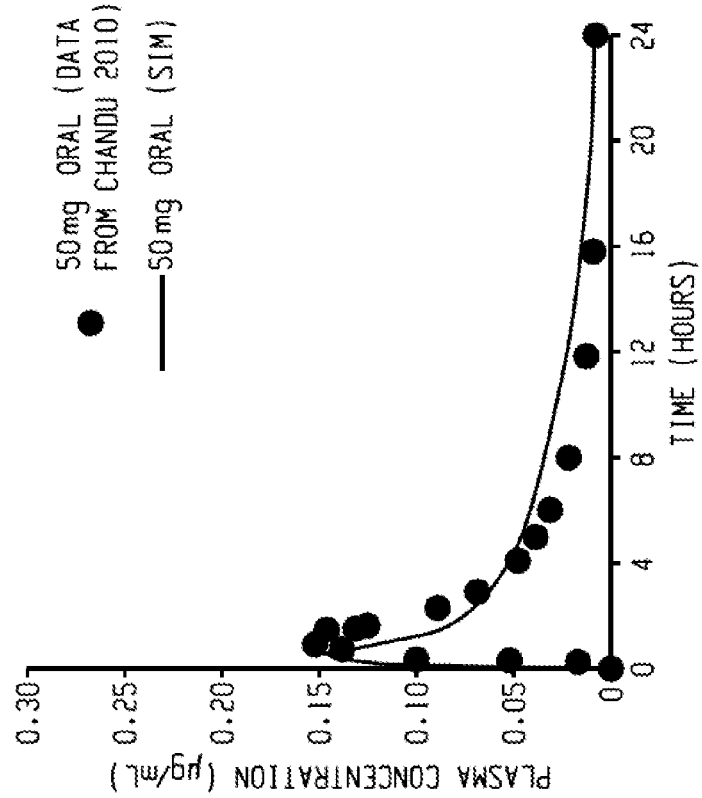
FIG. 5 illustrates the simulated and observed plasma concentrations of riluzole after a single 50 mg oral dose for observed data and data reported in Chandu et al (*Anal Bioanal Chem.* 2010)
Figure 5B:
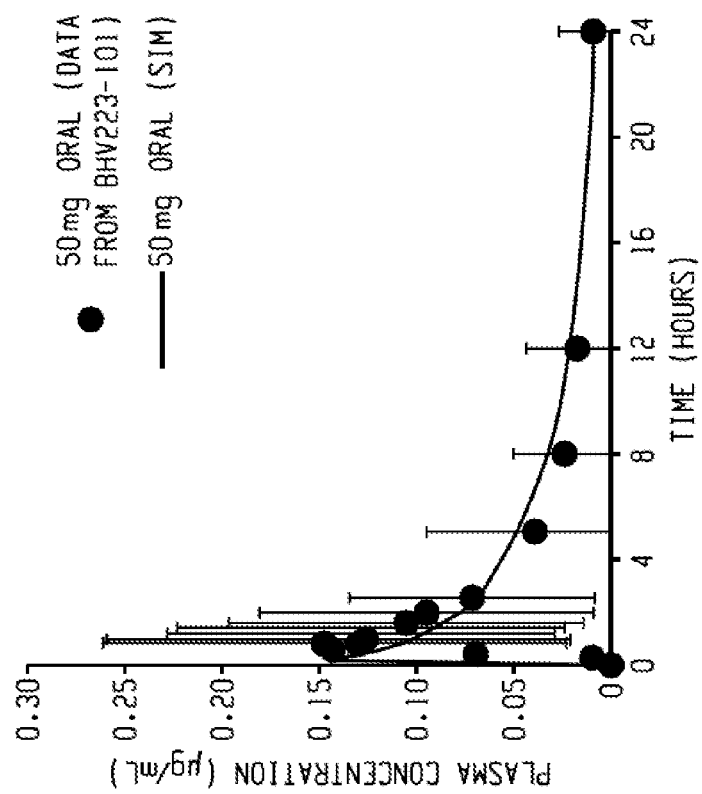

The DILIsym simulations reasonably captured the plasma PK of riluzole (FIGS. 4-5).

FIG. 4 shows Simulated (lines) and observed[a] (symbols) plasma concentrations of riluzole following (A) a single 100 mg oral dose and (B) a single 50 mg IV dose.

FIG. 5 shows Simulated (lines) and observed (symbols) plasma concentrations of riluzole after a single 50 mg oral dose for (A) observed data from the phase 1 study of BHV-0223 and (B) data reported in Chandu et al (*Anal Bioanal Chem.* 2010)

Simulations in which 0% of a 35 mg sublingual dose of riluzole was absorbed via the oral mucosa and 100% passed through the GI tract underestimated observed plasma concentrations following a single 35 mg sublingual dose.

Riluzole Toxicity Simulation

In the SimPops simulations, no ALT elevations >3×ULN were predicted for either dosing protocol (oral or sublingual) with median PK and high or default liver exposure assumptions (Table 9).

TABLE 9

Simulated frequency of ALT elevations in SimPops administered riluzole

| Riluzole dose and duration | DILIsym parameter settings | Simulated ALT > 3 × ULN[a] | Simulated ALT > 5 × ULN[a] |
|---|---|---|---|
| Oral 50 mg once daily for 12 weeks | Median PK, liver $K_b$ 10 | 0/285 | 0/285 |
| | High PK, liver $K_b$ 10 | 11/285 | 3/285 |
| Sublingual 40 mg once daily for 12 weeks | Median PK, liver $K_b$ 10 | 0/285 | 0/285 |
| | High PK, liver $K_b$ 10 | 4/285 | 2/285 |

[a]ULN in DILIsym is 40 U/L.
ALT, alanine aminotransferase;
$K_b$, liver-to-blood partition coefficient;
PK, pharmacokinetic;
ULN, upper limit of normal.

In the simulation with high PK and high liver exposure, the predicted incidence of ALT elevations was higher for oral dosing (11 of 285 individuals) vs sublingual dosing (4 of 285).

Findings from the SimCohorts simulations were similar: no ALT elevations were predicted with the default liver $K_b$ assumption combined with either median or high PK parameter; elevations were predicted only with the higher liver $K_b$ assumptions (Table 10).

TABLE 10

Simulated frequency of ALT elevations in SimCohorts administered riluzole

| Riluzole dose and duration | DILIsym parameter settings | Simulated ALT > 3 × ULN[a] | Simulated ALT > 5 × ULN[a] |
|---|---|---|---|
| Oral 50 mg once daily for 12 weeks | Median PK, liver $K_b$ 10 | 0/16 | 0/16 |
| | High PK, liver $K_b$ 10 | 3/16 | 1/16 |
| | Median PK, liver $K_b$ 35 | 3/16 | 1/16 |
| | High PK, liver $K_b$ 35 | 16/16 | 16/16 |
| Sublingual 40 mg once daily for 12 weeks | Median PK, liver $K_b$ 10 | 0/16 | 0/16 |
| | High PK, liver $K_b$ 10 | 1/16 | 1/16 |
| | Median PK, liver $K_b$ 35 | 1/16 | 1/16 |
| | High PK, liver $K_b$ 35 | 16/16 | 15/16 |

[a]ULN in DILIsym is 40 U/L.
ALT, alanine aminotransferase;
$K_b$, liver-to-blood partition coefficient;
PK, pharmacokinetic;
ULN, upper limit of normal.

In both simulations with high PK parameters and liver $K_b$ of 10 and in simulations with median PK and liver $K_b$ of 35, 3 of 16 simulated individuals with oral dosing and 1 of 16 individuals with sublingual dosing showed ALT elevations.

With high PK parameters and the highest liver $K_b$ value of 35, all simulated individuals in both dosing protocols had elevated ALT 3×ULN.

Conclusions

Sublingually administered BHV-0223 is associated with meaningful levels of mucosal absorption of riluzole, based on PBPK modeling.

While both deliver bioequivalent exposures, sublingual BHV-0223 theoretically has less risk of liver toxicity compared to riluzole oral tablets. This advantage is supported by DILIsym, which combines a mechanistic, quantitative representation of hepatotoxicity with inter-individual variability in both susceptibility and liver exposure.

DILIsym modeling demonstrated that sublingual BHV-0223 confers diminished rates of liver toxicity compared to oral tablets of riluzole, consistent with having a lower overall dose of riluzole and bypassing first-pass liver metabolism.

Key determinants of the simulated outcomes included liver exposure relative to plasma. Physiologically reasonable assumptions regarding liver exposure confirmed Part B Usefulness of Population Pharmacokinetic Modeling and Simulations in Predicting Bioequivalence: BVH-0223, a Case Example Objectives:

BHV-0223 is a sublingual formulation of riluzole designed to optimize pre-gastric absorption as compared to RILUTEK tablet. The objective was to determine the optimal dose of BHV-0223 and sample size for achieving bioequivalence (BE) with RILUTEK 50 mg using population pharmacokinetic (PK) and simulations.

Methods:

Data from 10 healthy subjects of Phase I study were used to develop a basic population PK model of riluzole. The validated population PK model was then used to simulate 50 BE studies with different doses of BHV-0223 and sample sizes. Predicted and observed area under the curve (AUC) and maximum concentration ($C_{max}$) were calculated using a non-compartmental method. Ratio and 90% confidence interval (CI) were calculated on ln-transformed AUCs and $C_{max}$. The success rate was computed as the percentage of simulated 90% CI within 80-125%. The results from these simulations were used to design the study conducted in Example 2.

Figure 6:
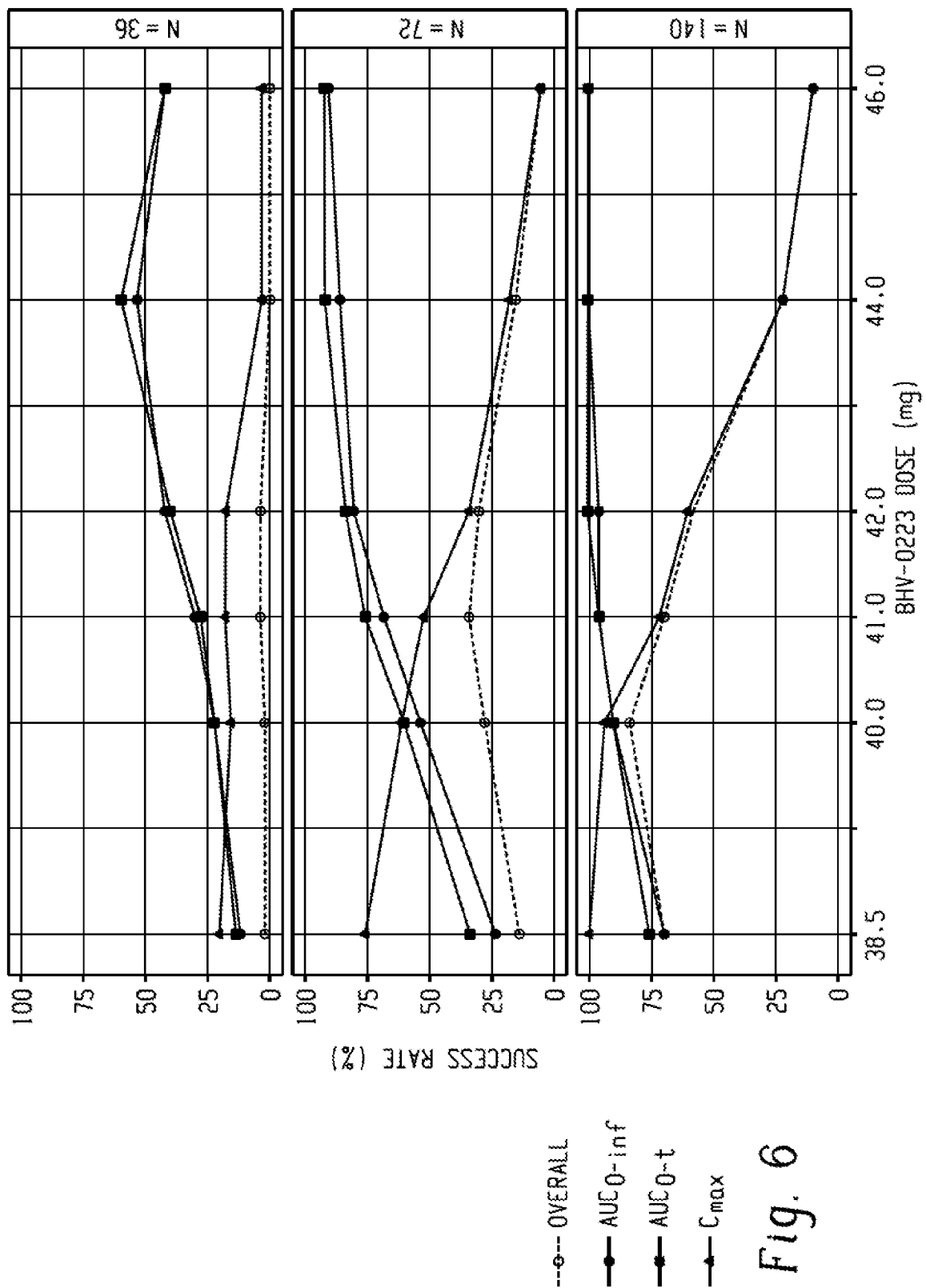
FIG. 6 illustrates bioequivalence success rates versus different doses of BHV-0223.

Results: A two-compartment model with first order absorption, lag time, and linear elimination provided the best fit for riluzole PK. The model parameters were estimated separately for BHV-0223 and Rilutek. Based on the simulations performed using this model, the best overall success rate (84%) was achieved with a dose of 40 mg and sample size of 140 subjects (FIG. 6). While BHV-0223 tends to have lower AUCs but a greater $C_{max}$ than Rilutek, it was possible to optimally balance the two goals with this dose. The BE criteria were actually met in study BHV0223-102 as the 90% geometric CI of ln-transformed AUCs, and $C_{max}$ were respectively 87% to 92% and 106% to 120%, with 132 subjects included in the analysis, fully in line with the predictions.

Conclusions: The population PK model adequately predicted that the BHV-0223 40 mg sublingual formulation is bioequivalent to Rilutek 50 mg tablet.

Example 4

Open-Label Study to Evaluate Safety and Tolerability of Sublingually Administered BHV-0223 Orally Disintegrating Tablets in Participants with Amyotrophic Lateral Sclerosis with Dysphagia Objective:

The primary objective of this study was to assess safety and tolerability of BHV-0223 in participants with ALS who have dysphagia. The secondary objectives of this study were to evaluate satisfaction, ease of use, and preference for BHV-0223. This study is sometimes referred to herein as BHV0223-104.

Methodology:

The BHV-0223 ODT is referred to as a BHV-0223 Zydis® sublingual formulation in the sections below. This was a Phase 1, open-label, single arm, single dose study to evaluate the safety and tolerability of sublingually administered BHV-0223 in subjects with ALS who have dysphagia, including those who are not currently taking riluzole tablets due to dysphagia and those who have been taking riluzole tablets but are now having difficulty taking the medication due to dysphagia.

The study consisted of a screening visit, dosing visit and follow up assessment. The screening and dosing visits could occur on the same day. Participants taking riluzole tablets were instructed to abstain from the morning dose of riluzole on the day of the dosing visit. Eligible participants received a single 40 mg dose of BHV-0223 administered sublingually under observation by the clinician/study personnel. Successful completion of study drug administration was evaluated using the clinician/study team questionnaire (CSTQ) to be completed by the clinician/staff who observed study drug administration. The study evaluated satisfaction with, ease of use as well as preference for sublingually administered BHV-0223 compared to standard riluzole tablets using the patient study questionnaire (PSQ), which was to be completed between 90-120 minutes after study drug administration.

A follow up phone call was to be conducted, within 3 days (between 24-72 hours after administration of study medication) from the end of the dosing visit, to assess the status of the participant.

Duration of Treatment:

This was a single-dose study. The subjects were observed and monitored by study personnel at the site for 2 hours after study drug administration. The site was to follow up with the subject via phone, within 3 days after the dosing visit to ask the subject to report any signs/symptoms experienced since the dose of BHV-0223 was administered. Accordingly, the minimum duration of study participation was planned to be 2 days (1 day for screening/dosing and 1 day for follow up assessment by phone) and the maximum duration of study participation was planned to be 18 days (1 day for screening, 14 day window for dosing, and 3 day window for follow up assessment by phone).

Safety:

The primary endpoint of this study was safety and tolerability as measured by frequency and severity of adverse events (AEs) and by CSTQ. The secondary endpoint was PSQ on satisfaction, ease of use, and medication preference. Safety variables included AEs, serious adverse events (SAEs), vital sign measurements, and physical examinations. No laboratory assessments were collected in this study; however, laboratory test results that met the definition of an SAE, or required discontinuation of study drug or if the subject received specific corrective therapy were documented.

Other:

Other assessments included the ALS functional rating scale-revised (ALSFRS-R), a clinician rated measure used to assess the functional status of subjects with ALS, and the eating assessment tool-10 (EAT-10), a subject reported measure used to assess dysphagia severity, were administered by clinician/site staff.

Statistical Methods:

The sample size for this study was 14 subjects. There were no power considerations in determining this sample size, however the probability of observing a specific adverse event would be approximately 80% if the true probability of this event occurring were 10%. Categorical variables were tabulated with counts and percentages. Continuous variables were summarized with univariate statistics (e.g. n, mean, standard error [SE], median, minimum, and maximum).

The primary endpoint, CSTQ was presented using a frequency table (i.e. yes or no) for whether study drug administration was successfully completed and listed by subject. The secondary endpoint, PSQ on satisfaction, ease of use, and preference, was presented using a frequency table (all other questions were also be presented in this table). A data listing was provided by question and by subject. Adverse events (AEs) were coded using the medical dictionary for regulatory activities (MedDRA version 20.0) coding system. Frequency tables were presented summarizing deaths, serious AEs (SAEs), AEs leading to discontinuation, and treatment emergent AEs (TEAEs)/treatment-related TEAEs, by severity. A by subject listing was generated for all AEs.

For ALSFRS-R (0=lowest possible score; 48=highest possible score) and EAT-10 (0=lowest possible score; 40=highest possible score) assessments, the total scores were summarized for each subject. Data listings of each question and overall total score were provided by subject.

Summary of Results:

Disposition and Baseline/Demographic Characteristics:

Fourteen (14) subjects were screened and were administered sublingual BHV-0223 (40 mg) formulation. All of the 14 treated subjects completed the study.

The median age was 71.5 years, the majority of subjects were male (64.3%), and all were white (100.0%). The mean subject age was 69.9 years and ranged from 58 to 82 years. Mean subject height was 172.0 cm, weight was 74.3 kg and BMI was 25.7 kg/m2.

All 14 subjects were diagnosed with ALS and had a history of dysphagia, defined as ALSFRS-R Item 3 (swallowing) scores of 3 (early eating problems-occasional choking; n=6), 2 (dietary consistency changes; n=3), or 1 (needs supplemental tube feeding, n=5). The mean ALSFRS-R score was 28 (SE=2.2) with a range from 13 to 4. Higher scores indicate a higher level of physical functioning. The mean total EAT-10 score was 15 (SE=3.3) with a range from 1 to 39. Higher scores indicate more severe dysphagia. At the time of screening, 7 subjects (50.0%) were currently taking riluzole tablets. All 7 of these subjects reported swallowing whole riluzole tablets with liquid, rather than taking crushed riluzole tablets. Amongst the 7 subjects (50.0%) who were not currently taking riluzole, 1 subject reported not taking riluzole tablets due to difficulty swallowing and the burden of the fasting requirement.

Primary Endpoint Results:

Study drug administration was successfully completed in all 14 subjects based on the CSTQ.

Other Results:

A high-level summary of PSQ results is listed below.

When questioned about satisfaction with the study medication, 11 subjects (78.6%) were either very satisfied (5 subjects, 35.7%) or satisfied (6 subjects, 42.9%); whereas, 3 subjects (21.4%) were dissatisfied. No subjects (0%) were very dissatisfied.

When questioned about ease of use, 13 subjects (92.9%) reported that the study medication was very easy (9 subjects, 64.3%) or easy (4 subjects, 28.6%) to use; whereas 1 subject (7.1%) reported that it was difficult. No subjects (0%) reported that it was very difficult.

When questioned about overall medication preference taking all factors into consideration, including any potential TEAEs, 8 subjects (57.1%) preferred BHV-0223 over the standard, whole riluzole tablet; 5 subjects (35.7%) preferred the standard, whole riluzole tablet over BHV-0223; and 1 subject (7.1%) had no preference for either tablet.

The level of physical disability measured by the ALSFRS-R and severity of dysphagia assessed by the EAT-10 were generally similar between the subgroups of subjects who had an overall preference for BHV-0223 and those who had an overall preference for standard, whole riluzole tablets. For the subgroup of 8 subjects who preferred BHV-0223 over the standard, whole tablets, mean ALSFRS-R and EAT-10 scores were 28.5 and 14.1, respectively. For the subgroup of 5 subjects who preferred the standard, whole tablets over BHV-0223, mean ALSFRS-R and EAT-10 scores were 25.4 and 17.4, respectively. There was 1 subject who was dissatisfied and had difficulty with the use of BHV-0223. This subject had a baseline ALSFRS-R score of 13 indicating the highest level of physical disability amongst all 14 subjects in the study (mean ALSFRS-R score=28, SE=2.2). Additionally, this subject had a baseline EAT-10 score of 24 in comparison to all 14 subjects in the study (mean EAT-10 score=15, SE=3.3). This subject did not experience any TEAEs.

Conclusions

BHV-0223 was successfully administered to all 14 ALS subjects with dysphagia, and there were no safety concerns.

The majority of subjects were very satisfied or satisfied with BHV-0223.

The majority of subjects found BHV-0223 to be very easy or easy to use.

More subjects preferred BHV-0223 over standard riluzole tablets than those who preferred standard riluzole tablets over BHV-0223, taking all factors into consideration, including any potential TEAEs.

Example 5

Open-Label Study to Evaluate Safety, Tolerability, and Pharmacokinetics of Multiple Doses of BHV-0223 in Subjects with Amyotrophic Lateral Sclerosis (BHV0223-103)

Methodology

This was a multiple-dose, open-label, multi-center study to assess safety, tolerability and pharmacokinetic (PK) of BHV-0223 40 mg sublingual formulation in subjects with Amyotrophic Lateral Sclerosis (ALS). The study was conducted in an outpatient basis. The screening period was expected to last up to a maximum of 28 days. In the treatment period, subjects were expected to receive BHV-0223 for approximately 8 weeks (57 days) in duration. The study drug was to be taken twice daily (approximately every 12 hours) for 8 weeks. Physical examinations, vital signs, and laboratory assessments for liver function testing were to be performed to assess safety and tolerability and PK measurements were to be collected to assess riluzole concentrations after multiple doses. AEs were to be closely monitored.

Number of Subjects Analyzed

Twenty-one (21) subjects were enrolled and were administered with at least one dose of sublingual BHV-0223 (40 mg) formulation. Data from all 21 subjects were analyzed.

Main Criteria for Inclusion

Males and females, 18 years of age and older, diagnosed with ALS and subjects who had never taken riluzole tablets, or those who previously took riluzole tablets but discontinued at least 1 month prior to the screening visit. Subjects with diagnosed ALS by the revised El Escorial diagnostic criteria, including laboratory supported probable, probable, or definite ALS.

Test Product, Dose, and Mode of Administration

Sublingual tablets of BHV-0223 40 mg, to be used twice daily basis (approximately every 12 hours), for approximately 2 months in total.

Criteria for Evaluation

This was a safety and tolerability study. Safety: The key safety variables included deaths, serious adverse events (SAEs), AEs, AEs leading to discontinuation, and laboratory abnormalities. The exploratory endpoints included ALS Functional Rating Scale Revised (ALSFRS-R) and oral tolerability assessments, and PK assessments.

Statistical Methods

Safety analyses were based on the treated population. The primary analysis included the frequency for deaths, SAEs, AEs, AEs leading to discontinuation. Treatment-emergent adverse event (TEAE) was defined as any new untoward medical occurrence or worsening of a pre-existing medical condition in a subject or clinical investigation subject administered an investigational (medicinal) product and that does not necessarily have a causal relationship with this treatment. The AEs were coded using the Medical Dictionary for Regulatory Affairs (MedDRA version 21.0) coding system. Laboratory measurements of hematology, serum chemistry, follicle stimulating hormone level, and urine pregnancy results at screening were listed. The laboratory abnormalities on LFTs (e.g. AST, ALT, GGT, ALP, direct and total bilirubin) were listed through approximately Day 57, and mean change from baseline, and potential drug induced liver toxicity (PDILI) was assessed. PDILI was defined as: Aminotransferases (ALT or AST) elevation >3× the upper limit of normal (ULN) and total bilirubin >2×ULN, without initial findings of cholestasis (elevated serum alkaline phosphatase) and no other immediately apparent possible causes of aminotransferase elevation and hyperbilirubinemia, including but not limited to, viral hepatitis, pre-existing chronic or acute liver disease, or the administration of other drug(s) known to be hepatotoxic. For vital signs, summary statistics (n, mean, standard error, minimum, median, and maximum) were presented for the change from baseline (defined as Day 1) values. Prior and concomitant medications were summarized (n and %) by ATC class Level 4 and preferred term. Summary statistics (n, mean, standard error, minimum, median, and maximum) were presented for the ALSFRS-R total score. For oral tolerability assessments, severity was summarized by frequency for each area inspected. Plasma riluzole concentrations were summarized by study day and collection time.

Summary of Results

Disposition and Baseline/Demographic Characteristics:

Twenty-one (21) subjects were enrolled and were administered with at least one dose of sublingual BHV-0223 (40 mg) formulation. Fifteen (71.4%) treated subjects completed the 8-week study period. Six (28.6%) subjects discontinued due to AEs.

The mean age was 61.7 years, there were similar number of male and female subjects in the study, and majority of subjects were white (90.5%). The mean height was 172.2 cm, mean weight was 74.5 kg, and mean BMI was 25.2 kg/m². All 21 subjects were diagnosed with ALS and the median ALSFRS-R total score was 37.0 (range 19 to 46). Eight (38.1%) subjects had used riluzole in the past.

In this study, subjects were expected to receive 40 mg BHV-0223 as twice daily for approximately 8 weeks. The median number of days of exposure was 56 days (mean 47.4 days range: 8 to 64 days). The 6 subjects who discontinued the study drug, had exposure to BHV-0223 for approximately 8 to 43 days.

Subjects were provided a 70-day supply of study drug over the course of the study. The median number of tablets used in the study was 112 (mean 94.5 tablets, range 16 to 128 tablets).

Safety Results:

In this study, multiple 40 mg doses of sublingually administered BHV-0223 were well tolerated in subjects with ALS. No new safety signals were observed with BHV-0223 as compared to the reference listed drug Rilutek (riluzole, 50 mg tablet).

There were no deaths or SAEs in this study.

Six (28.6%) subjects had 39 TEAEs that led to discontinuation of study drug. The TEAEs leading to discontinuation were consistent with those commonly associated with the tolerability of riluzole (i.e., asthenia [fatigue], nausea, vomiting, vertigo [dizziness], somnolence, paresthesia [numbness]).

Treatment-emergent AEs were reported in all 21 subjects (100%) who received at least one dose of BHV-0223.

The majority of subjects; (20/21, 95.2%) had TEAEs that were gastrointestinal in nature. The most frequently (in more than 2 [10%] subjects) reported TEAEs were oral hypoesthesia in 18 (85.7%) subjects, oral paraesthesia in 6 (28.6%) subjects, nausea in 6 (28.6%) subjects, fatigue in 4 (19.0%) subjects, dizziness in 4 (19.0%) subjects, and dry mouth in 3 (14.3%) subjects. All 6 subjects who reported oral paraesthesia also had oral hypoesthesia, implying a single interrelated phenomenon of oral numbness and tingling.

In total, 82 TEAEs were reported in 21 subjects, of these, 64 TEAEs reported in 20 (95.2%) subjects and were considered related to study drug by the investigator.

All TEAEs were mild to moderate in intensity, except for events of ALT and AST increase in 1 subject which were considered severe and moderate in intensity, respectively.

Aside from the severe LFT abnormalities experienced by 1 subject (was reported as a non-serious AE), there were no other clinically meaningful changes in laboratory values identified in this study.

There were no cases of PDILI in the study.

There were no discontinuations due to LFT abnormalities.

One subject (mentioned above) had ALT and AST levels change from normal at baseline to high at the end of study (ALT on Day 57:3.9×ULN [Retest: 3.6×ULN]; AST on Day 57:2.4×ULN [Retest: 2.0×ULN]). The subject had normal levels of LFTs at baseline and up to the Day 29 visit. These LFT levels were monitored after the end of the study and returned to normal at Day 114.

There were no clinically meaningful changes from baseline in vital signs and physical measurements.

Although oral hypoesthesia was the most frequently (85.7%) reported TEAE, the oral tolerability assessments indicated no clinically important, lasting effects of multiple doses of BHV-0223. No oral tolerability findings were attributed to BHV-0223.

Following BHV-0223 40 mg twice daily, the mean (percent coefficient of variation [% CV]) predose plasma riluzole concentration on Day 29 and 57 were 36,292 (63.9%) and 40,819 (59.8%) pg/mL, respectively. The mean (% CV) postdose plasma riluzole concentration on Day 1, 29 and 57 were 192,414 (34.8%), 270,226 (35%), and 236,969 (30.1%) pg/mL, respectively, suggesting no meaningful accumulation after multiple dosing.

Conclusions: Administration of multiple doses (twice daily for approximately 8 weeks) of 40 mg BHV-0223 sublingual formulation was well-tolerated in subjects with ALS as measured by the frequency of SAEs, AEs, AEs leading to discontinuation, and laboratory abnormalities on liver function testing. No new safety signals were observed with BHV-0223 as compared to the reference listed drug riluzole (Rilutek).

There were no deaths or SAEs in this study. This rate of discontinuation due to TEAEs in this study (28.6%) is consistent with rate of discontinuation observed in previous studies of riluzole. The TEAEs leading to discontinuation were consistent with those commonly associated with the tolerability of riluzole.

There were no cases of PDILI or clinically relevant changes in LFTs. Only 1 subject had an increase of ALT in the 3× to 5×ULN range that was reported as an AE. Such increases in ALT levels are expected events in a subset of subjects treated with riluzole and are the reason for the LFT monitoring requirement noted in the riluzole label.

Example 6

Video Fluoroscopic Swallowing Evaluation Study for Comparison of Swallowing Functions Before and After Administration of BHV-0223 (Riluzole Sublingual Dissolving Zydis®) Following a 40 Mg Dose in Healthy Subjects (BHV0223-105)

Primary Objective:

To compare the swallowing functions and any evidence of aspiration before and after a 40 mg BHV-0223 sublingual dissolving tablet administration in normal healthy volunteers.

Methodology

This was a single center, single-dose, open label, 1-period study to compare the swallowing functions and any evidence of aspiration before and after a 40 mg BHV-0223 sublingual dissolving tablet administration and to assess the safety and tolerability of BHV-0223 in normal healthy volunteers.

A total of 10 healthy adult male or female volunteers, 35 years of age and older, non-smoker, were planned to be dosed and evaluated for swallowing abilities. Subjects were enrolled in 2 groups of 5 subjects. Prior to entering the study, subjects had a screening visit to establish eligibility within 28 days before study drug administration. Subjects were confined to the inVentiv Clinical Research Facility from the evening of Day 1 until the morning of Day 2. On the morning of Day 1, subjects were transported to an external clinic for the visual fluoroscopic swallowing evaluation (VFSE) procedure and returned to the inVentiv clinic early in the afternoon. Subjects were accompanied by inVentiv staff during the transportation and the VFSE procedures. The total duration of the study for each subject was approximately 2 days.

Barium was administered in 4 consistencies and textures for the radiologic examination, ranging from liquid barium to barium-coated cookies (i.e. liquid barium, nectar-thick liquid barium, pudding-thick barium, and cookie-coated barium), in order to evaluate subject's ability to swallow in real time, before and after BHV-0223 administration. All eligible subjects received a single dose of 40 mg BHV 0223 to be held under the tongue for approximately 120 seconds without swallowing. Subjects swallowing functions were evaluated by VFSE (before and approximately 15 minutes after treatment administration). Each of the 4 different bolus type was presented twice to each subject (before and after dosing). This radiographic procedure provided a direct, dynamic view of oral, pharyngeal, and upper esophageal function.

The radiologist ensured that residual barium containing food had been evacuated before next swallowing. Following the VFSE baseline evaluation, subjects rinsed their mouth with water in order to remove any residual barium containing food.

| Treatment | |
|---|---|
| | Study Drug |
| Product | BHV-0223 40 mg Zydis ® sublingual formulation |
| Strength | 40 mg |
| Dosage form | Sublingual dissolving tablet |
| Dose administered | 1 × 40 mg |
| Route of administration | Sublingual |

A total of 10 healthy, adult male and female non-smokers were included in this study and received the following study drug:

Treatment: Riluzole 1×40 mg sublingual, dissolving Zydis® (BHV-0223, Biohaven Pharmaceuticals, Inc., USA)

A single-dose of BHV-0223 was placed under the subject's tongue and subjects were instructed to hold the sublingual tablet under the tongue for approximately 120 seconds without swallowing and not to crush or chew it. Then, a glass of water (240 mL) was consumed by the subject to ensure ingestion of all study medication.

Subjects were confined from the evening of Day-1 until the morning of Day 2. On the morning of Day 1, subjects were traveling to an outpatient clinic for the VFSE procedure and they returned to the clinic early in the afternoon. The total duration of the study for each subject was approximately 2 days.

Video Fluoroscopy Swallowing Evaluation (VFSE):

Subjects swallowing functions was evaluated by video fluoroscopy. Direct and dynamic view of oral, pharyngeal, and upper esophageal function was evaluated in real-time by a radiologist and the images were recorded for further review and analysis. The Dynamic Imaging Grade of Swallowing Toxicity (DIGEST) scale, which is based on the interaction of pharyngeal residue and laryngeal penetration/aspiration ratings, was used to assess the pharyngeal swallowing function.

Safety:

The safety and tolerability to BHV-0223 was evaluated through the assessment of adverse events (AEs), clinical laboratory parameters (biochemistry, hematology, and urinalysis), vital signs, and physical examination.

Swallowing Function Analyses:

For DIGEST total score, DIGEST efficiency score, and DIGEST safety score the number and percentage of subjects were tabulated per timepoint for each individual score (e.g. 0, 1, 2, 3, and 4). A summary table of shifts from baseline to post-dose measurements was provided for each DIGEST score.

Dynamic Imaging Grade of Swallowing Toxicity (DIGEST) Scale Results

The DIGEST scale was used to analyze VFSE data and assess swallowing function for the 10 subjects dosed with BHV-0223 in this study. All 10 subjects (100%) experienced TEAEs of hypoesthesia oral and were evaluated with VFSE while hypoesthesia oral was ongoing. None of the subjects in this study had objective evidence of dysphagia or aspiration at any timepoint (pre-dose or post-dose), based on the validated DIGEST scale (a subject is defined as having dysphagia on the DIGEST if they have a total score grade of 2 or more). Overall, there was no relevant difference in swallowing function before and after a 40 mg BHV-0223 sublingual dissolving tablet administration in normal healthy volunteers.

The data indicate that BHV-0223 had no clinically meaningful impact on swallowing efficiency. There were no subjects with any changes in DIGEST efficiency score from pre-dose to post-dose VFSE. One out of 10 subjects (Subject 08; 10.0%) had a DIGEST efficiency score of E1 on both the pre-dose and the post-dose VFSE. On the pre-dose VFSE, Subject 08 had 10-49% pharyngeal residue, on each of the 4 bolus types administered, which translated into a pre-dose DIGEST efficiency score of E1. On the post-dose VFSE, Subject 08 had 10-49% pharyngeal residue on 2 bolus types (nectar-thick liquid barium and cookie coated barium) and <10% pharyngeal residue on the other 2 other bolus types (liquid barium and pudding-thick barium), which also translated into a DIGEST efficiency score of E1. These types of mild abnormalities are known to occur in healthy subjects and are not deemed to be clinically meaningful. This subject did not experience a TEAE of dysphagia.

The data further indicate that BHV-0223 had no clinically meaningful impact on swallowing safety. One (1) out of 10 subjects (Subject 03 10.0%) had a DIGEST safety score of S0 on pre-dose VFSE that shifted to S1 on post-dose VFSE. On the pre-dose VFSE, Subject 03 had penetration-aspiration scale (PAS) scores of 1 (material does not enter the airway), on each of the 4 bolus types administered, which translated into a pre-dose DIGEST safety score of S0.

Throughout this application, various publications are referenced by author name and date, or by patent number or patent publication number. The disclosures of these publications are hereby incorporated in their entireties by reference into this application in order to more fully describe the state of the art as known to those skilled therein as of the date of the invention described and claimed herein. However, the citation of a reference herein should not be construed as an acknowledgement that such reference is prior art to the present invention.

Those skilled in the art will recognize, or be able to ascertain using no more than routine experimentation, numerous equivalents to the specific procedures described herein. Such equivalents are considered to be within the scope of this invention and are covered by the following claims. Furthermore, it is intended that specific items within lists of items, or subset groups of items within larger groups of items, can be combined with other specific items, subset groups of items or larger groups of items whether or not there is a specific disclosure herein identifying such a combination.

What is claimed is:

1. A method of treating cerebellar ataxia in a patient in need thereof, comprising administering to the patient a pharmaceutical composition comprising 50-70% riluzole, 15-25 weight % gelatin, 10-20 weight % mannitol, and 0.1-2 weight % docusate sodium, based on the total weight of the pharmaceutical composition, in the form of an oral solid molded fast-dispersing dosage form in order to provide an $AUC_{0-t}$ of from about 80-125% of about 740000 hr*pg/mL, wherein the dosage of riluzole in the oral solid molded fast dispersing tablet is from 50 to 90% of the dosage of riluzole in a conventional tablet in order to provide an $AUC_{0-t}$ of about 740000 hr*pg/mL.

2. The method of claim 1, wherein the dosage of riluzole in the oral solid molded fast dispersing tablet is from 70 to 85% of the dosage of riluzole in a conventional tablet in order to provide an $AUC_{0-t}$ of about 740000 hr*pg/mL.

3. The method of claim 2, wherein the dosage of riluzole in the oral solid molded fast dispersing tablet is about 80% of the dosage of riluzole in a conventional tablet in order to provide an $AUC_{0-t}$ of about 740000 hr*pg/mL.

4. The method of claim 1, wherein the dosage of riluzole in the oral solid molded fast dispersing tablet is about 40 mg.

* * * * *